(12) United States Patent
Usuka et al.

(10) Patent No.: US 7,698,117 B2
(45) Date of Patent: *Apr. 13, 2010

(54) SYSTEM AND METHOD FOR PREDICTING CHROMOSOMAL REGIONS THAT CONTROL PHENOTYPIC TRAITS

(75) Inventors: Jonathan A. Usuka, Palo Alto, CA (US); Andrew Grupe, Redwood City, CA (US); Gary Allen Peltz, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/015,167

(22) Filed: Dec. 11, 2001

(65) Prior Publication Data

US 2002/0137080 A1    Sep. 26, 2002

Related U.S. Application Data

(63) Continuation-in-part of application No. 09/737,918, filed on Dec. 15, 2000.

(51) Int. Cl.
G06G 7/48 (2006.01)
G06G 7/58 (2006.01)
G01N 33/48 (2006.01)
G01N 31/00 (2006.01)

(52) U.S. Cl. .............................. 703/11; 702/19; 702/20; 703/12

(58) Field of Classification Search .................... 702/20, 702/27; 707/1
See application file for complete search history.

(56) References Cited

U.S. PATENT DOCUMENTS

| | | | |
|---|---|---|---|
| 5,492,547 A | 2/1996 | Johnson et al. | |
| 5,581,657 A | 12/1996 | Lyon | |
| 6,123,451 A | 9/2000 | Schaefer et al. | |
| 6,132,724 A * | 10/2000 | Blum | 424/725 |
| 6,291,182 B1 | 9/2001 | Schork et al. | 435/6 |
| 6,303,115 B1 | 10/2001 | Natsoulis | |
| 2002/0119451 A1 * | 8/2002 | Usuka et al. | 435/6 |

FOREIGN PATENT DOCUMENTS

| | | |
|---|---|---|
| EP | 01 99 1144 | 9/2006 |
| WO | WO 97/48822 | 12/1997 |

OTHER PUBLICATIONS

Satagopan et al., Genetics, vol. 144, pp. 805-816, 1996.*
Almasy et al., Am. J. Hum. Genet., vol. 62, pp. 1198-1211, 1998.*
Buetow et al., 1991, "A detailed multipoint map of human chromosome 4 provides evidence for linkage heterogeneity and position-specific recombination rates," *Am. J. Hum. Genet.* 48:911-925.
Alison et al., 1998 "Multiple phenotype modeling in gene-mapping studies of quantitative traits: power advantages," *Am. J. Hum. Genet.* 63:1190-1201.
Amos et al., 1990 "A multivariate method for detecting genetic linkage, with application to a pedigree with an adverse lipoprotein phenotype," *Am. J. Hum. Genet.* 47:247-254.
Eisen et al., 1998 "Cluster analysis and display of genome-wide expression patterns," *Proc. Natl. Acad. Sci USA* 95:14863-14868.
Golub et al., 1999 "Molecular classification of cancer: class discovery and class prediction by gene expression monitoring," *Science* 286:531-537.
Machleder et al., 1997 "Complex genetic control of HDL levels in mice in response to an atherogenic diet," *J. Clin. Invest.* 99:1406-1419.
Olson et al., 1999 "Tutorial in biostatistics genetic mapping of complex traits," *Statist. Med.* 18:2961-2981.
Schadt et al., 1998 "Computational Advances in maximum likelihood methods for molecular phylogeny," *Genome Research* 8:222-233.
Schaid et al., 1994 "Comparison of statistics for candidate-gene associate studies using cases and parents," *Am. J. Hum. Genet.* 55:402-409.
Schork et al., 1998 "The future of genetic epidemiology," *TIG* 14: 266-272.
Weeks et al., 1995 "Polygenic disease: methods for mapping complex disease traits," *TIG* 11:513-516.
Risch, 2000, "Searching for genetic determinants in the new millennium," *Nature* 405:847-856.
Lynch et al., 1998 Ch. 15 "Mapping and Characterizing QTLs: Inbred Line Crosses", *Genetics and Analysis of Quantitative Traits*, Sinauer Associates, Inc. Publishers; 431-484.
Doerge, 2002, "Mapping and Analysis of Quantitative Trait Loci in Experimental Populations", *Nature* 3; 43-52.
Lynch et al., 1998 Ch. 1 "Foundations of Quantitative Genetics", *Genetics and Analysis of Quantitative Traits*, Sinauer Associates, Inc. Publishers; 1-17.
Lynch et al., 1998 Ch. 16 "Mapping and Characterizing QTLs: Outbred Populations", *Genetics and Analysis of Quantitative Traits*, Sinauer Associates, Inc. Publishers; 491-532.
Risch, "*Searching for Genetic Determinants in the New Millennium*," 2000, Nature 405, pp. 847-856.

(Continued)

*Primary Examiner*—Eric S DeJong
(74) *Attorney, Agent, or Firm*—Jones Day

(57) ABSTRACT

A method of associating a phenotype with one or more candidate chromosomal regions in a genome of an organism includes the step of deriving a phenotypic data structure that represents differences in phenotypes between different strains of the organism. Further, a genotypic data structure is established. The genotypic data structure corresponds to a locus selected from a plurality of loci in the genome of the organism. The genotypic data structure represents variations of at least one component of the locus between different strains of the organism. The phenotypic data structure is compared to the genotypic data structure to form a correlation value. The process of establishing a genotypic data structure and comparing it to the phenotypic data structure is repeated for each locus in the plurality of loci, thereby identifying one or more genotypic data structures that form a high correlation value relative to all other compared genotypic data structures. The loci that correspond to the one or more genotypic data structures having a high correlation value represent the one or more candidate chromosomal regions.

12 Claims, 15 Drawing Sheets

OTHER PUBLICATIONS

Lander and Schork, "*Genetic Dissection of Complex Traits,*" 1994, Science 265, pp. 2037-2048.

Tsao, "*Evidence for Linkage of a Candidate Chromosone 1 Region to Human Systemic Lupus Erythematosus,*" 1997, J. Clin. Invest. 99, pp. 725-731.

Tsao, "*PARP Alleles Within the Linked Chromosomal Region Are Associated With Systemic Lupus Erythematosus,*" 1999, J. Clin. Invest. 103, pp. 1135-1140.

Criswell et al., "*PARP Alleles and SLE: Failure to Confirm Association With Disease Susceptibility,*" 2000, J.Clin. Invest., 105, pp. 1501-1502.

Delrieu, et al., "*POLY(ADP-RIBOSE) Polymerase Alleles in French Caucasians Are Associated Neither With Lupus Nor With Primary Antiphospholipid Syndrome,*" 1999, Arthritis & Rheumatism 42, pp. 2194-2197.

Mucenski, et al., "*AKXD Recombinant Inbred Strains: Models for Studying the Molecular Genetic Basis Of Murine Lymphomas,*" 1986, Molecular & Cellular Biology 6, pp. 4236-4243.

Lindqvist, et al., "*A Susceptibility Locus for Human Systemic Lupus Erythematosus (hSLE1) on Chromosome 2g,*" 2000, Journal of Autoimmunity14, pp. 169-178.

Nadeau and Frankel, "*The Roads From Phenotypic Variation to Gene Discovery: Mutagenesis Versus QTLs,*" 2000, Nature Genetics 25, pp. 381-384.

Ewart, et al., "*Quantitative Trait Loci Controlling Allergen-Induced Airway Hyperresponsiveness in Inbred Mice,*" 2000, Am J. Respir. Cell Mol. Biol. 26, pp. 537-545.

Karp, et al., "*Identification of Complement Factor 5 As a Susceptibility Locus for Experimental Allergic Asthma,*" 2000, Nature Immunology 1, pp. 221-226.

Chrisp, et al., "*Lifespan and Lesions in Genetically Heterogeneous (Four-way Cross) Mice: A New Model for Aging Research,*" 1996, Veterinary Pathology 33, pp. 735-743.

Wielowieyski, et al., "*Tli1, A Resistance Locus for Carcinogen-Induced T-Lymphoma,*" 1999, Mammalian Genome 10, pp. 623-627.

Gilbert, et al., "*Susceptibility of AKXD Recombinant Inbred Mouse Strains to Lymphomas,*" 1993, J.Virol. 67, pp. 2083-2090.

Mucenski, et al., "*Identification of a Common Ecotropic Viral Integration Site, Evi-1, in the DNA of AKXD Murine Myeloid Tumors,*" 1988, Molecular & Cellular Biology 8, pp. 301-308.

Williams, et al., "*Natural Variation in Neuron Number in Mice is Linked to a Major Quantitative Trait Locus on Chr 11,*" 1998, Journal of Neuroscience 18, pp. 138-146.

Fisch, et al., "*A Generalization of the Mixture Model in the Mapping of Quantitative Trait Loci for Progeny from a Biparental Cross of Inbred Lines,*" 1996, Genetics 143 pp. 571-577.

Luo, et al., "*Interval Mapping of Quantitative Trait Loci in an F2 Population,*" 1992, Heredity 69 pp. 236-242.

Cox, et al., "*Loci on Chromosomes 2 (NIDDM1) and 15 Interact to Increase Susceptibility to Diabetes in Mexican Americans,*" Feb. 1999, Nature Genetics, vol. 21, pp. 213-215.

Jiang, et al., "*Mapping Quantitative Trait Loci With Dominant and Missing Markers in Various Crosses From Two Inbred Lines,*" 1997, Genetics, 101pp. 47-58.

Rozzo, et al., "*Evidence for an Interferon-Inducible Gene, Ifi202, in the Susceptibility to Systemic Lupus,*" Immunity, Sep. 2001, vol. 15 pp. 435-443.

Grupe, et al., "*In Silico Mapping of Complex Disease-Related Traits in Mice,*" ScienceReprint, Jun. 8, 2001, vol. 292 pp. 1915-1918.

Tsunoda, 2000, "Medical Informatics using SNP," Trials for Medication of New Century III—Bioinformatics accelerating Genome Science vol. 4. No. 3, with English translation.

Nadeau et al., 2000, "The roads from phenotypic variation to gene discovery: mutagenesis versus QTLs," Nature Genetics 25: 381-384.

Lanza et al., 1997, "Genetic distance of inbred lines and prediction of maize single-cross performance using RAPD markers," Theoretical and Applied Genetics, vol. 94: pp. 1023-1030.

PCT Written Opinion for PCT/US01/48524, mailing date Dec. 24, 2003, citing PCT publication WO/ 97/48822, 7 pp.

* cited by examiner

SYSTEM AND METHOD FOR PREDICTING CHROMOSOMAL REGIONS THAT CONTROL PHENOTYPIC TRAITS

CROSS REFERENCE TO RELATED APPLICATION

This application is a continuation-in-part of U.S. application Ser. No. 09/737,918, filed Dec. 15, 2000, which is incorporated by reference herein in its entirety.

COMPUTER PROGRAM LISTING APPENDIX

One compact disc that includes a Computer Program Listing Appendix has been submitted in duplicate in the present application. The size of the files contained in the Computer Program Listing Appendix, their date of creation, their time of creation, and their name are found in Table 1 below. In Table 1, each row represents a file or directory. If the row represents a directory, the designation "<DIR>" is provided in column one. If the row represents a file, the size of the file in bytes is provided in column one. Columns two and three respectively represent the date and time of file or directory creation while the fourth column represents the name of the file or directory.

TABLE 1

Table 1. Contents of the Computer Program Listing Appendix

| Size | Date of Creation | Time of Creation | File Name |
| --- | --- | --- | --- |
| 32,366 | 12-10-01 | 3:35 pm | Digidisease.pl |
| 33,987 | 12-10-01 | 3:36 pm | Display_dev.pm |
| 11,837 | 12-10-01 | 3:36 pm | Input_output_dev.pm |
| 6,583 | 12-10-01 | 3:36 pm | Locus_matrix.pl |
| 5,141 | 12-10-01 | 3:35 pm | Matrix_generator.pl |

The Computer Program Listing Appendix disclosed in Table 1 is hereby incorporated by reference.

BACKGROUND OF THE INVENTION

Identification of genetic loci that regulate susceptibility to disease has promised insight into pathophysiologic mechanisms and the development of novel therapies for common human diseases. Family studies clearly demonstrate a heritable predisposition to many common human diseases such as asthma, autism, schizophrenia, multiple sclerosis, systemic lupus erythematosus, and type I and type II diabetes mellitus. For a review, see Risch, Nature 405, 847-856, 2000. Over the last 20 years, causative genetic mutations for a number of highly penetrant, single gene (Mendelian) disorders such as cystic fibrosis, Huntington's disease and Duchene muscular dystrophy have been identified by linkage analysis and positional cloning in human populations. These successes have occurred in relatively rare disorders in which there is a strong association between the genetic composition of a genome of a species (genotype) and one or more physical characteristics exhibited by the species (phenotype).

It was hoped that the same methods could be used to identify genetic variants associated with susceptibility to common diseases in the general population. For a review, see Lander and Schork, Science 265, 2037-2048, 1994. Genetic variants associated with susceptibility to subsets of some common diseases such as breast cancer (BRCA-1 and -2), colon cancer (FAP and HNPCC), Alzheimer's disease (APP) and type II diabetes (MODY-1, -2, -3) have been identified by these methods, which has raised expectations. However, these genetic variants have a very strong effect in only a very limited subset of individuals suffering from these diseases (Risch, Nature, 405, 847-856, 2000).

Despite considerable effort, genetic variants accounting for susceptibility to common, non-Mendelian disorders in the general population have not been identified. Since multiple genetic loci are involved, and each individual locus makes a small contribution to overall disease susceptibility, it will be quite difficult to identify common disease susceptibility loci by applying conventional linkage and positional cloning methods to human populations. Mapping of disease susceptibility genes in human populations has also been hampered by variability in phenotype, genetic heterogeneity across populations, and uncontrolled environmental influences. The variable reports of linkage between the chromosome 1q42 region and systemic lupus erythematosus illustrate the difficulties encountered in human genetic studies. One group reported strong linkage between the 1q42 region (Tsao, J. Clin. Invest, 99, 725-731, 1997) and to microsatellite alleles of a gene (PARP) within that region (Tsao, J. Clin. Invest. 103, 1135-1140, 1999). In contrast, no evidence for association with the PARP microsatellite marker was noted (Criswell et al., J. Clin. Invest, June; 105, 1501-1502, 2000; Delrieu et al., Arthritis & Rheumatism 42, 2194-2197, 1999); and minimal (Mucenski, et al., Molecular & Cellular Biology 6, 4236-4243, 1986) or no linkage (Lindqvist, et al., Journal of Autoimmunity, March; 14, 169-178, 2000) to the 1q42 region was found in several other SLE populations analyzed. It is likely that additional tools and approaches will be needed to identify genetic factors underlying common human diseases.

Analysis of experimental murine genetic models of human disease biology should greatly facilitate identification of genetic susceptibility loci for common human diseases. Experimental murine models have the following advantages for genetic analysis: inbred (homozygous) parental strains are available, controlled breeding, common environment, controlled experimental intervention, and ready access to tissue. A large number of murine models of human disease biology have been described, and many have been available for a decade or more. Despite this, relatively limited progress has been made in identifying genetic susceptibility loci for complex disease using murine models. Genetic analysis of murine models requires generation, phenotypic screening and genotyping of a large number of intercross progeny. Using currently available tools, this is a laborious, expensive and time-consuming process that has greatly limited the rate at which genetic loci can be identified in mice, prior to confirmation in humans. For a review, see Nadeau and Frankel, Nature Genetics August; 25, 381-384, 2000.

The difficulties encountered in associating phenotypic variations, such as susceptibility to common diseases, with genetic variations gives rise to a need in the art for additional tools for identifying chromosomal regions that are most likely to contribute to quantitative traits or phenotypes. In view of this situation, it would be highly desirable to provide a technique for associating a phenotype with one or more candidate chromosomal regions in the genome of an organism without reliance on time consuming techniques such as cross breeding experiments or laborious post-PCR manipulation.

SUMMARY OF THE INVENTION

The present invention provides a system and method for associating a phenotype with one or more candidate chromosomal regions in the genome of an organism. In the method, phenotypic differences between a plurality of strains of the organism are correlated with variations and/or similarities in the respective genomes of the plurality of strains of the organism. The invention relies on the use of a genotypic database that includes variations and similarities of representative strains of the organism of interest. Representative genotypic databases include, but are not limited to, single nucleotide polymorphism databases, microsatellite marker databases, restriction fragment length polymorphism databases, short tandem repeat databases, sequence length polymorphism databases, expression profile databases, and DNA methylation databases.

One embodiment of the present invention provides a method for associating a phenotype with one or more candidate chromosomal regions in a genome of an organism. In this method, a phenotypic data structure that represents a difference in one or more phenotypes between different strains of the organism is derived. In its simplest form, the phenotypic data structure comprises a definition of one or more phenotypes exhibited by the organism together with a measure of each of these phenotypes. For example, a hypothetical phenotypic data structure for rabbits could include the phenotypes "tail length" and "hair color" and the respective measure for each of these phenotypes could be "7 centimeters" and "brown."

A genotypic data structure is established in accordance with one embodiment of the present invention. The genotypic data structure is identified by a particular locus selected from a plurality of loci present in the genome of the organism. The genotypic data structure includes one or more positions within the locus. For each of these positions, the genotypic data structure provides information on the extent of a variation between different strains of the organism. A hypothetical example of a genotypic data structure in accordance with the present invention is a data structure for a locus that includes genes A and B. In such an example, the genotypic data structure includes the positions of genes A and B within the locus as well as some measurement related to genes A and B, such as the mRNA expression level that has been measured for each of these genes. In this example, the mRNA expression-level defines the extent of variation between different strains of the organism.

The phenotypic and genotypic data structures are then compared to form a correlation value. The process continues with the establishment of another genotypic data structure that corresponds to a different loci and the concomitant comparison of this genotypic data structure to the phenotypic structure until several of the loci in the genome of the organism have been tested in this manner. In this way, one or more genotypic data structures are identified that form a high correlation value relative to all other genotypic data structures that have been compared to the phenotypic data structure. Further, the loci in the genome of the organism that correspond to the highly correlated genotypic data structures represent one or more candidate chromosomal regions that may be associated with the phenotype of interest.

In some embodiments of the present invention, each element in a phenotypic data structure represents a variation in the phenotype between a different first and second strain of the organism of interest. Such variations may be determined by measurement of an attribute corresponding to the phenotype in the respective strains of the organism. Representative phenotypic variations include, for example, eye color, hair color, and susceptibility to a particular disease. In other embodiments, each element in a phenotypic data structure represents a variation in the phenotype between a different first and second cluster of strains of the organism of interest.

In additional embodiments of the present invention, the genotypic data structure represents a variation of at least one component of a locus between two strains of the organism of interest. In other embodiments, each element in the genotypic data structure represents a variation of at least one component of the locus between a different first cluster of strains of the organism and a different second cluster of strains of the organism. In some embodiments, the phenotypic and genotypic data structures represent a subset of all strains of the organism of interest.

The present invention contemplates a considerable number of different methods for comparing the phenotypic and genotypic data structures. In one embodiment the correlation value between the phenotypic data structure and a particular genotypic data structure is formed in accordance with the expression:

$$c(P, G^L) = \frac{\sum^i (p(i) - \langle P \rangle)(g(i) - \langle G^L \rangle)}{\left\{ \left[ \sum^i (p(i) - \langle P \rangle)^2 \right] \left[ \sum^i (g(i) - \langle G^L \rangle)^2 \right] \right\}^{1/2}}$$

where, $c(P, G^L)$ is the correlation value;

$p(i)$ is a value of the $i^{th}$ element of the phenotypic data structure;

$g(i)$ is a value of the $i^{th}$ element of the genotypic data structure;

$\langle P \rangle$ is a mean value of all elements in the phenotypic data structure;

$\langle G^L \rangle$ is a mean value of all elements in the genotypic data structure; and $$\sum^i = \sum_{i=1}^N, \text{ where}$$

N is equal to a number of elements in the genotypic data structure.

Other methods for forming a correlation value between the phenotypic data structure and a particular genotypic data structure include but are not limited to regression analysis, regression analysis with data transformations, a Pearson correlation, a Spearman rank correlation, a regression tree and concomitant data reduction, partial least squares, and canonical analysis.

In some embodiments of the present invention, statistical methods are used to identify which of the genotypic data structures that have been compared to a phenotypic data structure are highly correlated. In one such embodiment, a mean correlation value that represents a mean of correlation values is computed between the phenotypic data structure and a particular genotypic data structure. Further, a standard deviation of the mean correlation is computed. Genotypic data structures having a correlation value that is a number of standard deviations above the mean correlation value are considered to be the data structures that correspond to loci that are associated with the genotypic trait. The number of standard deviations that is chosen for the cutoff is dynamically chosen so that a specific percentage of the genome, such as ten percent, is identified as positive.

Another aspect of the present invention provides a method of determining a portion of a genome of an organism that is responsive to a perturbation. In this aspect of the present invention, a first phenotypic data structure is produced that represents a difference in a first phenotype between different strains of the organism. The first phenotype is measured for each of the different strains of the organism when each different strain is in a first state. Then, a genotypic data structure is established. The genotypic data structure corresponds to a locus selected from a plurality of loci within the genome of the organism. Further, the genotypic data structure represents a variation, between different strains of the organism, of at least one component of the selected locus. The first phenotypic data structure is compared to the genotypic data structure to form a correlation value. These establishing and comparing steps are repeated for each locus in the plurality of loci. In this way a first set of genotypic data structures is identified that form a high correlation value relative to all other genotypic data structures evaluated in iterations of the comparing step.

Then, a second phenotypic data structure is constructed that represents a difference in a second phenotype between different strains of the organism. The second phenotype is measured for each of the different strains of the organism when each of the different strains are in a second state that is produced by exposing the different strains of the organism to a perturbation. The second phenotypic data structure is correlated to the genotypic data structure to form a correlation value. The computing and correlating steps are repeated for each locus in the plurality of loci thereby identifying a second set of genotypic data structures that forms a high correlation value relative to all other genotypic data structures that are evaluated during the correlating step. Finally, a dissimilarity in the first set of genotypic data structures and the second set of genotypic structures is resolved, thereby determining the portion of the genome of the organism that is responsive to the perturbation.

BRIEF DESCRIPTION OF THE DRAWINGS

Like reference numerals refer to corresponding parts throughout the several views of the drawings.

DETAILED DESCRIPTION OF THE INVENTION

Figure 1:
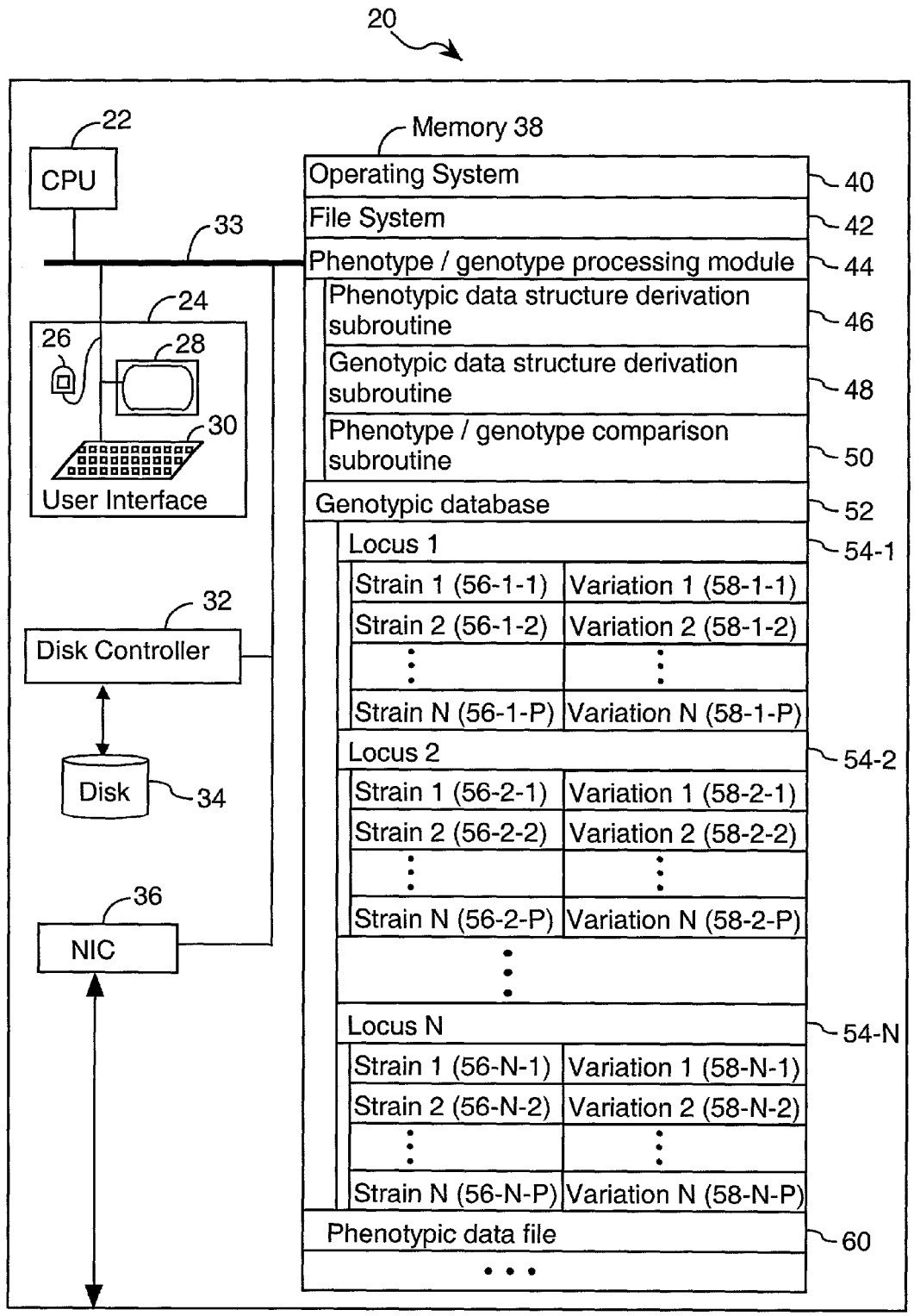
FIG. 1 illustrates a computer system for associating a phenotype with one or more candidate chromosomal regions in a genome of an organism in accordance with one embodiment of the present invention.

A key aspect of research in genetics is associating sequence variations with heritable phenotypes. The most common variations are single nucleotide polymorphisms (SNPs), which occur approximately once every 100 to 300 bases in a genome. Because SNPs are expected to facilitate large-scale association genetics studies, there has recently been great interest in SNP discovery and detection. The present invention contemplates the use of genotypic databases such as SNP databases in order to correlate genetic variances in an organism with one or more phenotypic variances. As an example, a searchable database of mouse SNPs that contains alleles for 15 common inbred mouse strains and information for performing high throughput, inexpensive genotyping assays for each SNP was built. Using pooled DNA samples and SNP genotyping assays in the database, a genome scan on phenotypically extreme progeny from an experimental intercross was completed. SNP-based genotyping of pooled samples requires at least twenty-fold fewer assays than genotyping individual samples with microsatellite markers, and identified the same linkage regions.

Although the examples provided herein utilize a genotypic database that includes fifteen mouse strains, it will be appreciated that the methods of the present invention allow of the use of any number of different types of genetic information. For example, suitable genotypic databases include databases that have various types of gene expression data from platform types such as spotted microarray (microarray), high-density oligonucleotide array (HAD), hybridization filter (filter) and serial analysis of gene expression (SAGE) data. Another example of a genetic database that can be used is a DNA methylation database. For details on a representative DNA methylation database, see Grunau et al., "MethDB—a public database for DNA methylation data," Nucleic Acids Research 29: 270-274, 2001.

Gene expression changes often reflect genotypic variation. Therefore, databases of gene expression among tissues obtained from different individuals (mouse strains or humans), can also be utilized by this method. The chromosomal position of all human genes is known for human genes, as a result of physical mapping or sequencing of the human genome. For gene expression data for mouse or other species, the chromosomal location is either known (physical mapping or mouse genomic sequencing) or can be estimated by syntenic mapping based upon homology with human genes.

To accelerate the process of analyzing experimental genetic models in order to identify the genetic causes of complex human disease, the present invention provides tools for scanning genotypic databases, such as SNP databases, to predict quantitative trait loci (QTL) after phenotypic information obtained from common strains of the organism is provided. The computational QTL prediction method is capable of correctly predicting the chromosomal regions that have been previously identified by tedious and laborious analysis of experimental intercross populations for the multiple traits that are analyzed. Thus, the present invention bypasses the burdensome requirement for generation and characterization of intercross progeny, enabling QTL regions to be predicted within a millisecond time frame.

FIG. 1 shows a system 20 for associating a phenotype with one or more candidate chromosomal regions in a genome of an organism.

System 20 preferably includes:

a central processing unit 22;

a main non-volatile storage unit 34, preferably a hard disk drive, for storing software and data, the storage unit 34 controlled by disk controller 32;

a system memory 38, preferably high speed random-access memory (RAM), for storing system control programs, data, and application programs, including programs and data loaded from non-volatile storage unit 34; system memory 38 may also include read-only memory (ROM);

a user interface 24, including one or more input devices (26, 30) and a display 28;

a network interface card 36 for connecting to any wired or wireless communication network; and an internal bus 33 for interconnecting the aforementioned elements of the system.

Operation of system 20 is controlled primarily by operating system 40, which is executed by central processing unit 22. Operating system 40 may be stored in system memory 38. In a typical implementation, system memory 38 includes:

operating system 40;

file system 42 for controlling access to the various files and data structures used by the present invention;

phenotype/genotype processing module 44 for associating a phenotype with one or more candidate chromosomal regions in a genome of an organism;

genotypic database 52 for storing variations in genomic sequences of a plurality of strains of an organism; and phenotypic data 60 that includes measured differences in one or phenotypic traits associated with the organism.

In a preferred embodiment, phenotype/genotype processing module 44 includes:

a phenotypic data structure derivation subroutine 46 for deriving a phenotypic data structure that represents a variation in a phenotype between different strains of an organism of interest;

a genotypic data structure derivation subroutine 48 for establishing a genotypic data structure that corresponds to a locus in the genome of the organism of interest; and a phenotype/genotype comparison subroutine 50 for comparing the phenotypic array to the genotypic array to form a correlation value.

The operation of these subroutines is described below in connection with the description for FIG. 2.

Genotypic database 52 is any type of genetic database that tracks variations in the genome of an organism of interest. Information that is typically represented in genotypic database 52 is a collection of loci 54 within the genome of the organism of interest. For each locus 54, strains 56 for which genetic variation information is available are represented. For each represented strain 56, variation information 58 is provided. Variation information 58 is any type of genetic variation information. Representative genetic variation information 58 includes, but is not limited to, single nucleotide polymorphisms, restriction fragment length polymorphisms, microsatellite markers, restriction fragment length polymorphisms, and short tandem repeats. Therefore, suitable genotypic databases 52 include, but are not limited to:

| Genetic variation type | Uniform resource location |
|---|---|
| SNP | bioinfo.pal.roche.com/usuka_bioinformatics/cgi-bin/msnp/msnp.pl |
| SNP | snp.cshl.org/ |
| SNP | ibc.wustl.edu/SNP/ |
| SNP | www-genome.wi.mit.edu/SNP/mouse/ |
| SNP | ncbi.nlm.nih.gov/SNP/ |
| Microsatellite markers | informatics.jax.org/searches/polymorphism_form.shtml |
| Restriction fragment length polymorphisms | informatics.jax.org/searches/polymorphism_form.shtml |
| Short tandem repeats | cidr.jhmi.edu/mouse/mmset.html |
| Sequence length polymorphisms | mcbio.med.buffalo.edu/mit.html |
| DNA methylation database | genome.imb-jena.de/public.html |

In addition, the genetic variations used by the methods of the present invention may involve differences in the expression levels of genes rather than actual identified variations in the composition of the genome of the organism of interest. Therefore, genotypic databases 52 within the scope of the present invention include a wide array of expression profile databases such as the one found at the URL:

ncbi.nlm.nih.gov/geo/

It will be appreciated that when the variation tracked by genotypic database 52 is a variation in the expression level of a gene rather than a variation in the genome, there is no requirement that genomic database 52 be populated with elements such as locus 54.

Figure 2:
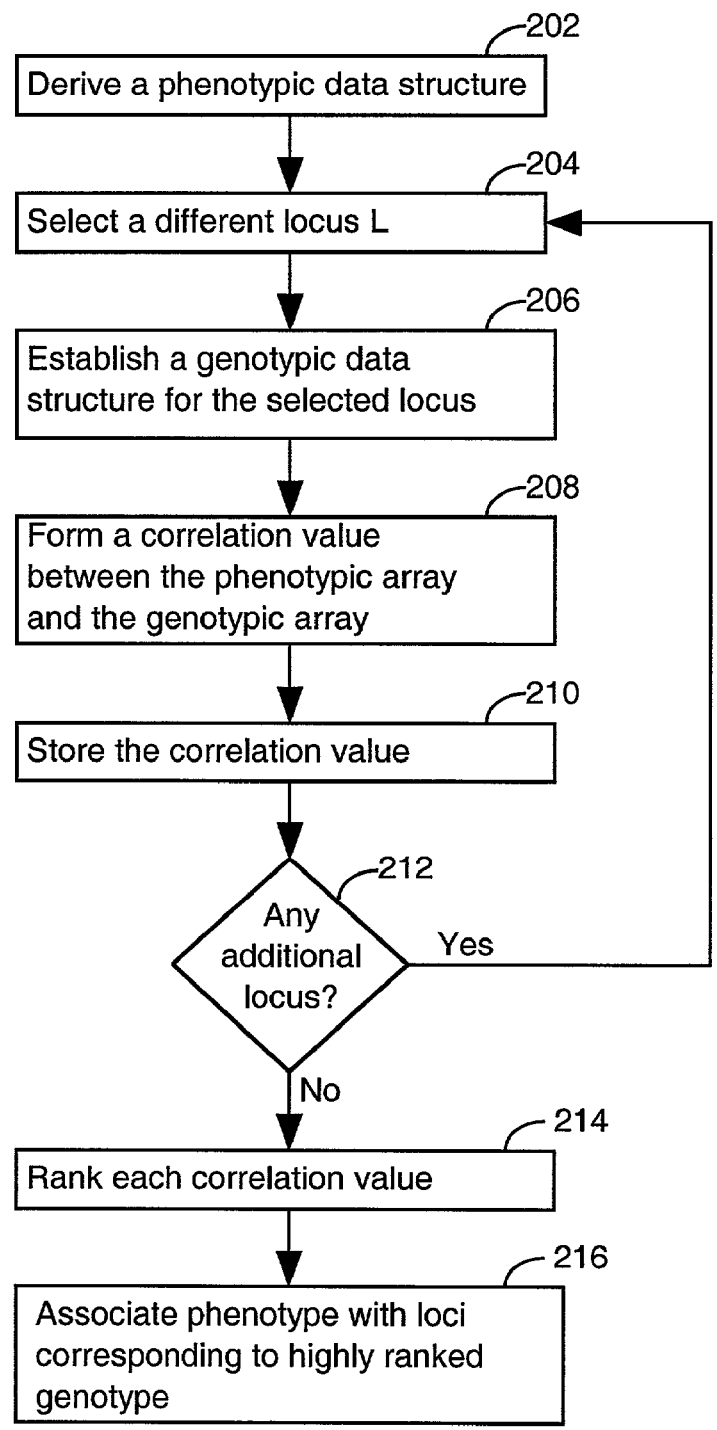
FIG. 2 illustrates the processing steps for associating a phenotype with one or more candidate chromosomal regions in a genome of an organism in accordance with one embodiment of the present invention.

Referring to FIG. 2, the processing steps that are performed in accordance with one embodiment of the present invention are illustrated. In processing step 202, a phenotypic data structure is derived from phenotypic data 60 (FIG. 1) using phenotypic data structure derivation subroutine 46 (FIG. 1). The phenotypic data structure tracks measured differences in traits between strains of an organism of interest.

In one embodiment, the phenotypic data structure used is a phenotypic array. In this embodiment, the phenotypic array is formed in a stepwise fashion by subroutine 46. First, an N×N phenotypic distance matrix, P, is established where both the ith row and the jth column are associated with a given strain for which quantitative information $t_i$ exists for a given trait.

This matrix is populated with the differences between strains in regard to the examined trait as follows:

$$P_{(i,j)} = |t_i - t_j|$$

Therefore, each element in the matrix corresponds to a distance between strains using the quantitative trait as a metric for the space. This matrix has the following properties:

All of its diagonal elements are zero, because $$P_{(i,i)} = |t_i - t_i| = 0 \forall i$$

The matrix is symmetric, because $$P_{(i,j)} = |t_i - t_j| = |t_j - t_i| = P_{(j,i)}$$

As an example, consider phenotypic information on the lifespan of five mouse strains:

| Strains | Lifespan (days) |
|---|---|
| A/J | 777 |
| AKR/J | 282 |
| C3H/HeJ | 510 |
| C57BL/6J | 895 |
| DBA/2J | 568 |

An exemplary phenotypic distance matrix that tracks the lifespan for these five species members has the form:

| P | A/J | AKR/J | C3H/HeJ | C57BL/6J | DBA/2J |
|---|---|---|---|---|---|
| A/J | 0 | 495 | 267 | 118 | 209 |
| AKR/J | 495 | 0 | 228 | 613 | 286 |
| C3H/HeJ | 267 | 228 | 0 | 385 | 58 |
| C57BL/6J | 118 | 613 | 385 | 0 | 327 |
| DBA/2J | 209 | 286 | 58 | 327 | 0 |

Each value in this illustrative phenotypic distance matrix represents the difference in life span between the designated members.

The phenotypic data structure derivation subroutine 46 converts the phenotypic matrix to the phenotypic array by taking the non-redundant, non-diagonal elements of the matrix and arranging them into a vector P:

$$P = P_{(1,2)}, P_{(1,3)}, \ldots, P_{(1,N)}, P_{(2,3)}, P_{(2,4)}, \ldots, P_{(2,N)}, \ldots P_{(N-1,N)}$$

The vector P obtained for the illustrative distance matrix set forth above is P=(495, 267, 118, 209, 228, 613, 286, 385, 58, 327). The linear format of P facilitates the ordered comparison of the phenotype and genotype of respective strains of an organism of interest in subsequent computational steps.

In some embodiments of the present invention, the phenotypic data used by phenotypic data structure derivation subroutine 46 (FIG. 1) in processing step 202 (FIG. 2) is entered by hand into system 20 by a computer operator. In other embodiments, the phenotypic data is read from a source such as phenotypic data file 60 (FIG. 1). It will be appreciated that there are no limitations on the format of the phenotypic data. The phenotypic data can, for example, represent a series of measurements for a quantifiable phenotypic trait in a collection of strains of a species. Such quantifiable phenotypic traits may include, for example, murine tail length, lifespan, eye color, size and weight. Alternatively, the phenotypic data can be in a binary form that tracks the absence or presence of some phenotypic trait. As an example, a "1" may indicate that a particular species of the organism of interest possesses a given phenotypic trait and a "0" may indicate that a particular species of the organism of interest lacks the phenotypic trait. The phenotypic data structure can be populated with any form of biological data that is representative of the phenotype of the organism of interest. Thus, in some embodiments of the present invention, the phenotypic data can be expression data such as MRNA expression data or protein expression level data. In such embodiments, each element in the phenotypic data structure is populated with differences in mRNA or protein expression levels between strains of the organism of interest or of cells cultured from the organism of interest.

In processing step 204, a particular locus is selected within the genome of the organism of interest. Processing step 204 is the first step of a repetitive loop formed by processing steps 204 through 212 that is repeated for several different loci, or positions, within the genome of the organism of interest. In some embodiments of the present invention, the size of the locus L that is selected in each instance of processing step 204 may be set to a specific size. For example, when the genotypic database 52 is a SNP database, the size of locus L is set to a predetermined number of centiMorgans (cM). Then, in each instance of processing step 204, a different locus having the predetermined number of cM is chosen. A centiMorgan is an art recognized unit of measure that quantifies the spatial relationship between positions within a chromosome. More specifically, a centiMorgan is a measure of genetic recombination frequency. One cM is equal to a one percent chance that a marker at one genetic position will be separated from a marker at another position due to crossing over in a single generation. In humans, 1 cM is equivalent, on average, to 1 million base pairs. In some embodiments, the size of the locus L selected in processing step 204 is less than 5 cM, 10 cM, 20 cM, 30 cM, 50 cM, 100 cM or a value greater than 100 cM.

It will be appreciated that units other than cM may be used to set the size of the locus L selected in each instance of processing step 204. For example, the size of the locus L may be set in units of nucleotides or even kilobases of nucleotides. In one embodiment, once the size of the locus has been initially set in a given session, each different locus L that is selected in subsequent instances of processing step 204 is chosen such that is has the same size as the locus L that was initially selected.

In processing step 206, a genotypic data structure is established for the selected locus. In one embodiment, processing step 206 is performed by genotypic data structure derivation subroutine 48 (FIG. 1). The genotypic data structure is typically formed in by a method similar to the construction of the phenotypic data structure. The values of the phenotypic data structure are typically the differences in quantitative traits exhibited by several strains of an organism of interest. In contrast, the values in the genotypic data structure correspond to counts of the polymorphic differences between strains for a given locus L that contains M genetic variations, such as SNPs. That is, a given locus L may have several independent genetic variations M, and the goal of the genotypic array that corresponds to this locus is to quantify the number of these independent genetic variations. To accomplish this, an individual variation matrix $S^x$ is established for each variation in every position x within locus L. In each such matrix, $S^x$, the $i^{th}$ row and the $j^{th}$ column are associated with the allele value $l^x(i)$ for strain i and the allele value $l^x(j)$ for strain j at locus position x according to the following rule:

$$S^x(i, j) = 1/2 \text{ if } l^x(i) = \emptyset \text{ or } l^x(j) = \emptyset$$
$$= 0 \quad \text{if } l^x(i) = l^x(j)$$
$$= 1 \quad \text{if } l^x(i) \neq l^x(j)$$

where $\emptyset$ indicates the allelic value for strain i at locus position x is not known at the present time. Therefore, if the alleles for two strains i and j are identical at position x, the entry in the individual variation matrix for x would be:

$$S^x(i,j) = S^x(j,i) = 0$$

and if the two alleles are different, a "1" is entered.

In some cases, not all allelic information is known at the present time (symbolized by $\emptyset$). For example, locus position x may contain information on the allele for strain i, but not for strain j. In this situation, the assumption is made that strain j has equal probability of containing either allele, and the corresponding entry is set equal to one half.

At this point, in some embodiments of the present invention, each individual variation matrix S contains elements that take on one of three values: 0, ½, or 1. It will be appreciated that many other types of schemes may be used when allelic information is not presently known and use of the value "½" in such instances merely illustrates one example of a scheme that is used in such instances. Similarly, any number of weighting schemes can be used rather than a "0" or "1" and all such weighting schemes are within the scope of the present invention.

In one embodiment of the invention, a variation matrix S that tracks an individual locus position x for five members (M1 through M5) of a species has the form:

| Illustrative variation Matrix S | | | | | |
|---|---|---|---|---|---|
| S | M1 | M2 | M3 | M4 | M5 |
| M1 | 0 | 0.5 | 0.5 | 1 | 0 |
| M2 | 0.5 | 0 | 0.5 | 0 | 1 |

| Illustrative variation Matrix S | | | | | |
|---|---|---|---|---|---|
| S | M1 | M2 | M3 | M4 | M5 |
| M3 | 0.5 | 0.5 | 0 | 1 | 1 |
| M4 | 1 | 0 | 1 | 0 | 0.5 |
| M5 | 0 | 1 | 1 | 0.5 | 0 |

In one embodiment of the present invention, in order to assemble the overall genotypic matrix for this locus, each individual variation matrix S within the locus L selected in processing step 204 is summed. To illustrate this concept, consider the case in which a locus L was selected in processing step 204 (FIG. 2). In this illustrative example, the locus L was selected using a 20 cM window, so the size of locus L is 20 cM. Further, there are five locus positions x in locus L. Each locus position x is represented by a corresponding variation matrix. In this case, therefore, the overall genotypic matrix g(i, j) for this locus is computed by summing the five variation matrices as follows:

$$g(i, j) = \sum_{m=5}^{5} g_m(i, j)$$

More generally, a given locus L will have M variations, each variation represented by a corresponding variation matrix S. Then, the overall genotypic matrix g(i, j) for the locus is computed using the expression:

$$g(i, j) = \sum_{m=5}^{M} g_m(i, j)$$

Therefore, an illustrative genotypic matrix G that represents a specific locus in five species members (M1 through M5) has the form:

| Illustrative Genotypic Matrix G | | | | | |
|---|---|---|---|---|---|
| G | M1 | M2 | M3 | M4 | M5 |
| M1 | 0 | 3.5 | 2 | 4 | 3 |
| M2 | 3.5 | 0 | 3 | 2.5 | 1 |
| M3 | 2 | 3 | 0 | 1 | 1 |
| M4 | 4 | 2.5 | 1 | 0 | 0.5 |
| M5 | 3 | 1 | 1 | 0.5 | 0 |

In viewing the illustrative genotypic matrix G above, it is apparent that there is relatively little genotypic variance between members M5 and M4 (0.5) whereas there is more variance between M1 and M2 (3.5).

In one aspect of the invention, each overall genotypic matrix G is assembled from individual component variation matrices S within locus L using a weighting scheme. Generally speaking, a weighting scheme in accordance with the present invention first identifies the center of the locus L that was selected in processing step 204. Variation matrices S that are close to the center of this locus receive full weight whereas variation matrices S that are far away from the center of locus L receive only partial weight. Thus, the weighting schemes in accordance with the present invention emphasize or upweight variation matrices S that are near the center of the selected locus L and deemphasize or downweight variation matrices that are far away from the center of the selected locus L. Weighting schemes in accordance with this aspect of the present invention are particularly advantageous when genotypic databases 52 (FIG. 2) such as SNP databases are used. This is because variation matrices S that are close to the center of locus L are more reliable than variation matrices S that are far from the center of locus L when such matrices are derived from SNP database data. Accordingly, the weighting scheme acts to emphasize more reliable data when the data is combined to form genotypic matrix G.

To illustrate the general principles of the weighting schemes in accordance with this aspect of the invention, consider the case where a genotypic matrix will be generated based upon two variation matrices, $S_1$ and $S_2$, that are found within a given locus L.

$S_1$ is located 5 cM from the center of locus L and has the values:

| Illustrative variation Matrix $S_1$ | | | | | |
|---|---|---|---|---|---|
| S | M1 | M2 | M3 | M4 | M5 |
| M1 | 0 | 0.5 | 0.5 | 1 | 0 |
| M2 | 0.5 | 0 | 0.5 | 0 | 1 |
| M3 | 0.5 | 0.5 | 0 | 1 | 1 |
| M4 | 1 | 0 | 1 | 0 | 0.5 |
| M5 | 0 | 1 | 1 | 0.5 | 0 |

$S_2$ is located 15 cM from the center of locus L and has the values:

| Illustrative variation Matrix $S_2$ | | | | | |
|---|---|---|---|---|---|
| S | M1 | M2 | M3 | M4 | M5 |
| M1 | 0 | 0.5 | 0.5 | 1 | 0 |
| M2 | 0.5 | 0 | 0.5 | 0 | 1 |
| M3 | 0.5 | 0.5 | 0 | 1 | 1 |
| M4 | 1 | 0 | 1 | 0 | 0.5 |
| M5 | 0 | 1 | 1 | 0.5 | 0 |

Because $S_2$ is located further away from the center of locus L, one filtering scheme in accordance with the present invention applies a weight of 0.5 to each element in $S_2$. Therefore, the genotypic matrix G that is derived from the combination of all positions x in locus L in this embodiment of the present invention will have the values:

database, the positions x in a given locus L can be approximated as a binomial distribution centered on the center of locus L. Thus, the distribution of locus positions x about the center of locus L may be fitted to a Gaussian probability distribution and each respective locus position x may be weighted by the probability for the respective locus position x that is derived from the Gaussian probability distribution. A Gaussian probability distribution weighting scheme is merely provided to demonstrate one form of weighting scheme that is used in some embodiments of the present invention. Many other forms of weighting schemes based on probability functions are possible. For example, Poisson distribution or Lorentzian distribution schemes may be used. See Bevington and Robinson, *Data reduction and error analysis for the physical sciences*, McGraw Hill, New York, New York, 1992.

In some embodiments of the present invention, processing step 206 further includes a correlation step in which each gene within the locus L selected in processing step 204 is allowed to contribute a maximum of one relative unit to genotypic matrix G. To illustrate embodiments of the present invention that are in accordance with this aspect of the invention, consider the case in which locus L has three positions $\ell$, $\ell$, and $\ell$, where $\ell$ and $\ell$ are in gene A and $\ell$ is in gene B. A corresponding variation matrix S is computed for each of the three locus positions. Then, because each gene is allowed to contribute only one relative unit to the genotypic matrix G, the variation matrix representing $\ell$ and the variation matrix representing $\ell$ are given half weight whereas the variation matrix representing $\ell$ is given full weight when the three variation matrices are summed to yield the corresponding genotypic matrix G.

Embodiments in which each gene within the locus L selected in processing step 204 is allowed to contribute a maximum of one relative unit provides an advantageous filtering effect when correlating phenotypic data to genotypic data in subsequent processing steps. Often, in any given genotypic database 52, there are some genes that have undergone several mutations and there are some genes that have undergone relatively few mutations, if any. After the first few mutations in any given gene have arisen, the informative value that subsequent mutations in the gene provide on localizing phenotypic traits to specific positions in chromosomes diminishes. In fact, as the number of mutations in a single gene becomes sufficiently large, the gene becomes overrepresented in phenotypic to genotypic correlation computations that are performed in the subsequent processing steps illustrated in FIG. 2. To see this, consider the case in which a given locus L has two genes A and B and the genotypic data for locus L is drawn from a SNP database in which there are ten

| S | M1 | M2 | M3 | M4 | M5 |
|---|---|---|---|---|---|
| M1 | 0 | 0.5 + ½(0.5) | 0.5 + ½(0.5) | 1 + ½(1) | 0 |
| M2 | 0.5 + ½(0.5) | 0 | 0.5 + ½(0.5) | 0 | 1 + ½(1) |
| M3 | 0.5 + ½(0.5) | 0.5 + ½(0.5) | 0 | 1 + ½(1) | 1 + ½(1) |
| M4 | 1 + ½(1) | 0 | 1 + ½(1) | 0 | 0.5 + ½(0.5) |
| M5 | 0 | 1 + ½(1) | 1 + ½(1) | 0.5 + ½(0.5) | 0 |

It will be appreciated that a broad number of different types of weighting schemes may be used to de-emphasize locus positions x that are far away from the center of locus L and to emphasize locus positions x that are proximate to the center of locus L. For example, when genotypic database 52 is a SNP SNPs for gene A and only one for gene B. If genes A and B are not constrained so that they contribute one relative unit to the genotypic matrix, gene A would have an order of magnitude more influence over gene B in subsequent correlation steps where phenotypic data is correlated to genotypic data. This can be seen by an example in which there are two strains of mice, M1 and M2, in which genes A and B are represented for M1 and M2 in a SNP database as follows:

M1: (1, 0); (2, 0); (3, 0); (4, 0); (5, 0); (6, 0); (7, 0); (8, 0); (9, 0); (10, 0); (11, 0)

M2: (1, 1); (2, 1); (3, 1); (4, 1); (5, 1); (6, 1); (7, 1); (8, 1); (9, 1); (10, 1); (11, 1)

In the SNP data representation above, each x coordinate represents a position in locus L and each y coordinate has a value of "0" when there is a polymorphism present at position x and a value of "1" when there is no polymorphism present at position x. In this example, positions 1-10 are located in gene A and position 11 is located in gene B. If genes A and genes B are allowed to contribute unequally to the genotypic matrix G, the genotypic matrix will have the values:

| Genotypic Matrix G Unequal contribution from genes A and B | | |
|---|---|---|
| G | M1 | M2 |
| M1 | 0 | 11 |
| M2 | 11 | 0 |

If genes A and genes B are constrained so that they contribute a maximum amount of one relative unit to the genotypic matrix, positions 1 through 10 will be weighted by 0.1 so that they contribute a total of 1. Thus, the genotypic matrix G will have the values:

| Genotypic Matrix G unequal contribution from genes A and B | | |
|---|---|---|
| G | M1 | M2 |
| M1 | 0 | 2 |
| M2 | 2 | 0 |

Imposing the constraint that each gene in a locus L contributes a single relative unit to the genotypic matrix has the advantage of preventing any given gene or sets of genes from dominating the correlation coefficient that is computed between phenotypic data and genotypic data in subsequent processing steps. There are several different ways to constrain the relative contribution of each gene within the locus L selected in processing step 204 so that any given gene does not overly dominate the corresponding genotypic matrix G. For example, genes could be constrained based on their length, where longer genes are allowed to contribute more than shorter genes. In another example, genes could be constrained based on percent A+T nucleotide content. In other schemes, genes that include more locus positions x in locus L are allowed to contribute more to the genotypic matrix than genes that include less locus positions x. However, the amount that such genes are allowed to contribute is not linearly proportional to the number of locus positions x within the gene. Rather, for example, the amount that a particular gene is allowed to contribute to the genotypic matrix is logarithmically proportional to the number of locus positions x in the gene.

In some embodiments of the present invention, two locus positions $L^1$ and $L^2$ in locus L are considered to be in the same gene if both positions map to a region of DNA that has been assigned the same accession number in a genetic database. Genetic databases include databases such as the Human Genome Database (GDB), Saccharomyces Genome Database (SGD), Mouse Genome Database (MGD), Drosophila Genetic Database (FLYBASE IMGT/LIGM) (ebi.ac.uk/embl/Documentation/User_manual/dr_line.html) or Genbank (ncbi.nlm.nih.gov/Genbank/). Many other genetic databases are known and are within the scope of the present invention.

Now that various embodiments used to construct genotypic matrices have been described, attention turns to how these matrices are used. One embodiment of genotypic data structure derivation subroutine 48 converts the genotypic matrix to a genotypic array by taking the non-redundant, non-diagonal elements of the matrix and arranging them into the vector G:

$$G = \mathcal{G}(1,2), \mathcal{G}(1,3), \ldots, \mathcal{G}(1,N), \mathcal{G}(2,3),$$
$$\mathcal{G}(2,4), \ldots, \mathcal{G}(2,N), \ldots \mathcal{G}(N-1,N)$$

The vector G obtained for the illustrative genotypic matrix set forth above is G=(3.5, 2, 4, 3, 3, 2.5, 1, 1, 1, 0.5). Once a genotypic matrix such as G has been established in processing step 206, a correlation value is formed between the phenotypic array and the genotypic array (processing step 208). This correlation value is typically computed by phenotype/genotype comparison subroutine 50 (FIG. 1). In one embodiment, this correlation is determined by linear regression correlation in which the correlation coefficient is calculated as:

$$c(P, G^L) = \frac{\sum^i (p(i) - \langle P \rangle)(g(i) - \langle G^L \rangle)}{\{[\sum^i (p(i) - \langle P \rangle)^2][\sum^i (g(i) - \langle G^L \rangle)^2]\}^{1/2}} \quad \text{Eqn. 1}$$

where, $c(P, G^L)$ is the correlation value between the phenotypic array and the genotypic array that corresponds to locus L;

$p(i)$ is a value of the $i^{th}$ element of the phenotypic array;

$\mathcal{G}(i)$ is a value of the ith element of the genotypic array;

<P> is a mean value of all elements in the phenotypic array;

<$G^L$> is a mean value of all elements in the genotypic array; and $$\sum^i = \sum_{i=1}^N \text{ where,}$$

N is equal to a number of elements in the genotypic array.

It will be appreciated that the phenotypic and genotypic arrays can be compared in processing step 208 using any number of algorithms other than linear regression. For example, alternative methods for forming a correlation value in processing step 208 include, but are not limited to, regression analysis, regression analysis with data transformations, Pearson correlations, Spearman rank correlation, a regression tree and concomitant data reduction, partial least squares, and canonical analysis. (See e.g. Lui, "Statistical Genomics," CRC Press LLC, New York, 1998; Stuart & Ord, "Kendall's Advanced Theory of Statistics," Arnold, London, England, 1994).

In some embodiments of the present invention, the correlation coefficient is weighted by the number of locus positions x in locus L. Such weighting is based on the observation that correlations $c(P, G^L)$ computed using a locus L that has a relatively large number of locus positions x receive a correlation coefficient that is artificially low relative to those correlations $c(P, G^L)$ that are computed using a locus L that has a relatively few number of locus positions x. To illustrate, consider a first correlation coefficient having the value of 0.5 that was computed using a locus L that includes 100 single nucleotide polymorphisms (SNPs) versus a second correlation coefficient having that value of 0.6 that was computed using a locus L that includes only 10 SNPs. The first correlation coefficient may have more significance because it was computed across a much larger number of SNPs.

It will be appreciated that weighting correlation coefficients $c(P, G^L)$ based on the number of locus positions x over which they are computed may be performed by any number of techniques and all such techniques are within the scope of the present invention.

One method of weighting involves computing a correlation coefficient for each locus L selected in processing step 204 using the expression:

$$c(P, G^L) = \frac{\left[\sum^i (p(i) - \langle P \rangle)(g(i) - \langle G^L \rangle)\right][n]^{1/2}}{\{[\sum^i (p(i) - \langle P \rangle)^2][\sum^i (g(i) - \langle G^L \rangle)^2]\}^{1/2}} \quad \text{Eqn. 2}$$

where, $c(P, G^L)$ is the correlation value between the phenotypic array and the genotypic array that corresponds to locus L;

$p(i)$ is a value of the $i^{th}$ element of the phenotypic array;

$g(i)$ is a value of the $i^{th}$ element of the genotypic array;

$\langle P \rangle$ is a mean value of all elements in the phenotypic array;

$\langle G^L \rangle$ is a mean value of all elements in the genotypic array;

n is the number of locus positions x in locus L; and $$\sum^i = \sum_{i=1}^{N} \text{ where,}$$

N is equal to a number of elements in the genotypic array.

It will be appreciated that Eqn. 2 may be derived from Eqn. 1 by multiplying the numerator of Eqn. 1 by the square root of n, where n is defined as the number of locus positions x in locus L for which a correlation $c(P, G^L)$ is being computed. It has been determined that, for some data sets, weighting $c(P, G^L)$ by the square root of n provides improved $c(P, G^L)$ values. While not intending to be limited to any particular theory, it is believed that Eqn. 2 corrects for an inherent bias against correlation coefficients computed for loci L, using Eqn. 1, that have a large number of locus positions x. Other forms of weighting based on number of locus positions x in locus L are possible. For example, rather than multiplying the numerator of Eqn. 1 by the square root of n (Eqn. 2), the numerator of Eqn. 1 could be multiplied by n, $n^2$, n raised to any power, log(n), ln(n), or $e^n$. One of skill in the art will recognize that other forms of weighting using n, the number of locus positions x in the locus L, are possible and all such weighting schemes are within the scope of the present invention. In some embodiments, the genotypic database 52 used is a SNP database and the number of positions x in the locus L are the number of SNPs in the SNP database within the given locus L.

In another embodiment of the present invention, linear regression or weighted linear regression is not used to determine a correlation coefficient. Instead, a correlative measure $cm$ is computed. A correlative measure $cm$ in accordance with this embodiment of the present invention is:

$$cm(P, G^L) = \frac{\left[\sum^i (p(i) - \langle P \rangle)(g(i) - \langle G^L \rangle)\right]}{\{[\sum^i (p(i) - \langle P \rangle)^2]\}^{1/2}} \quad \text{Eqn. 3}$$

where, $cm(P, G^L)$ is the correlation value between the phenotypic array and the genotypic array that corresponds to locus L;

$p(i)$ is a value of the $i^{th}$ element of the phenotypic array;

$g(i)$ is a value of the $i^{th}$ element of the genotypic array;

$\langle P \rangle$ is a mean value of all elements in the phenotypic array; and $\langle G^L \rangle$ is a mean value of all elements in the genotypic array.

While processing steps 202 through 206 have been described with reference to linear phenotypic and genotypic arrays, it will be appreciated that the methods of the present invention are not limited to the comparison of such arrays. Indeed, any form of data structure having elements that preserve the information in the above described matrices and arrays may be used. For example, rather than using the genotypic array described above, the individual variation matrices can be used. Further, rather than using the phenotypic array, a phenotypic distance matrix can be used.

Once a correlation value between the phenotypic data structure and a genotypic data structure that corresponds to a particular locus L has been formed, the correlation value is stored in processing step 210 so that it can be subsequently ranked with the correlation value of each of the other loci that are analyzed.

Processing step 212 is provided so that the procedure can be repeated in an iterative fashion for all suitable loci 54 in genotypic database 52 (FIG. 1). Thus, in processing step 212, a decision is made whether to test an additional locus by asking whether all of the loci present in genotypic database 52 (FIG. 1) have been tested. In one embodiment, when additional loci 54 are present in genotypic database 52, processing step 212 returns a "yes" and the process continues by looping back to processing step 204 where an additional, untested locus is selected from genotypic database 52.

In typical embodiments of the present invention, step 212 acts as a sliding scale. In such embodiments, an initial instance of processing step 204 picks a locus at a starting point on a particular chromosome in the organism of interest. The locus is considered a window. This window typically has a length that is measured in centiMorgans. Steps 204 through 210 are then performed for the window selected in processing step 204. This results in a correlation value for the window. Then, process control returns to step 204 where the window is incrementally advanced to a position along the chromosome that is contiguous with or even overlaps with a locus that was selected in a prior instance of processing step 204. This incremental advance may, for example, be a specified number of nucleotides or centiMorgans. When the specified number of nucleotides or centiMorgans is less than the window length, it follows that successive windows selected in each instance of processing step 204 will overlap with each other. The iterative process of selecting a window in processing step 204, computing the corresponding correlation value, and advancing the window continues until the end of the chromosome is reached. In organisms that have multiple chromosomes such as mice, this process continues for each chromosome until a window has been advanced over each chromosome in the organism. In one embodiment of the present invention, the window is advanced by 10 cM in each successive instance of processing step 204. However, this increment is readily adjustable.

In another aspect of the present invention, the window is advanced in each successive instance of processing step 204 by a step that approaches an infinitesimally small quantity. It has been found that such embodiments provide smoother output. Thus, in embodiments where the window is advanced by a very small incremental amount, the window is advanced by 2 cM, 1 cM, 0.1 cM, 0.01 cM or less.

In some embodiments of the present invention, processing step 214 does not compute a correlation value using linear regression. Rather, correlative measures using equations such as Eqn. 2 or Eqn. 3 are used. The use of a correlative measure rather than a correlation coefficient determined by linear regression does not affect other aspects of the present invention.

When there are no additional loci to test (212-No), the correlation value for each of the comparisons of genotypic data structures to the phenotypic data structure are ranked with respect to each other in processing step 214. In one embodiment, processing step 214 comprises the arrangement of the tested loci in a vector K according to their correlation scores:

$$K = (L^t, L^u, L^v, \ldots)$$

where $c(P, G^{L^t}) \geq c(P, G^{L^u}) \geq c(P, G^{L^v}) \geq \ldots$

In another embodiment of the present invention, processing step 214 includes the computation of (i) a mean correlation value that represents a mean of each correlation value formed during instances of processing step 208; and (ii) a standard deviation of the mean correlation value based on each of the correlation values formed during instances of processing step 208.

In processing step 216, the genotypic data structures that achieve the highest correlation values are selected. Since each genotypic data structure corresponds to a particular locus in the genome, the selection process in processing step 216 results in the association of the phenotype with particular loci in the organism of interest. In one embodiment, the selection process in processing step 216 is performed by selecting genotypic data structures that form a correlation value that is a predetermined number of standard deviations above the mean correlation value. Typically, the predetermined number is chosen so that a small percentage of the genome of the organism, such as five percent, will be selected during processing step 216.

In some embodiments of the present invention, phenotype/genotype processing module 44 (FIG. 2) includes a user interface. An exemplary user interface is illustrated in FIGS. 7-10. In some embodiments, the user interface allows the user to quickly toggle between a mode in which genotypic matrices are computed in an unweighted fashion, where each SNP is given equal weight, and a weighted fashion, where each accession number is given equal weight. One of skill in the art will appreciate that genotypic data is often characterized by accession numbers, where each accession number corresponds to a different gene in an organism of interest. Furthermore, in any given genotypic database, there will be several SNPs within any given gene. Therefore, each gene, or accession number, will include many SNPs. In fact, larger genes will have more SNPs. Thus, weighting by accession number (by gene) will produce a very different result then the case where each SNP is given equal weight.

Figure 7:
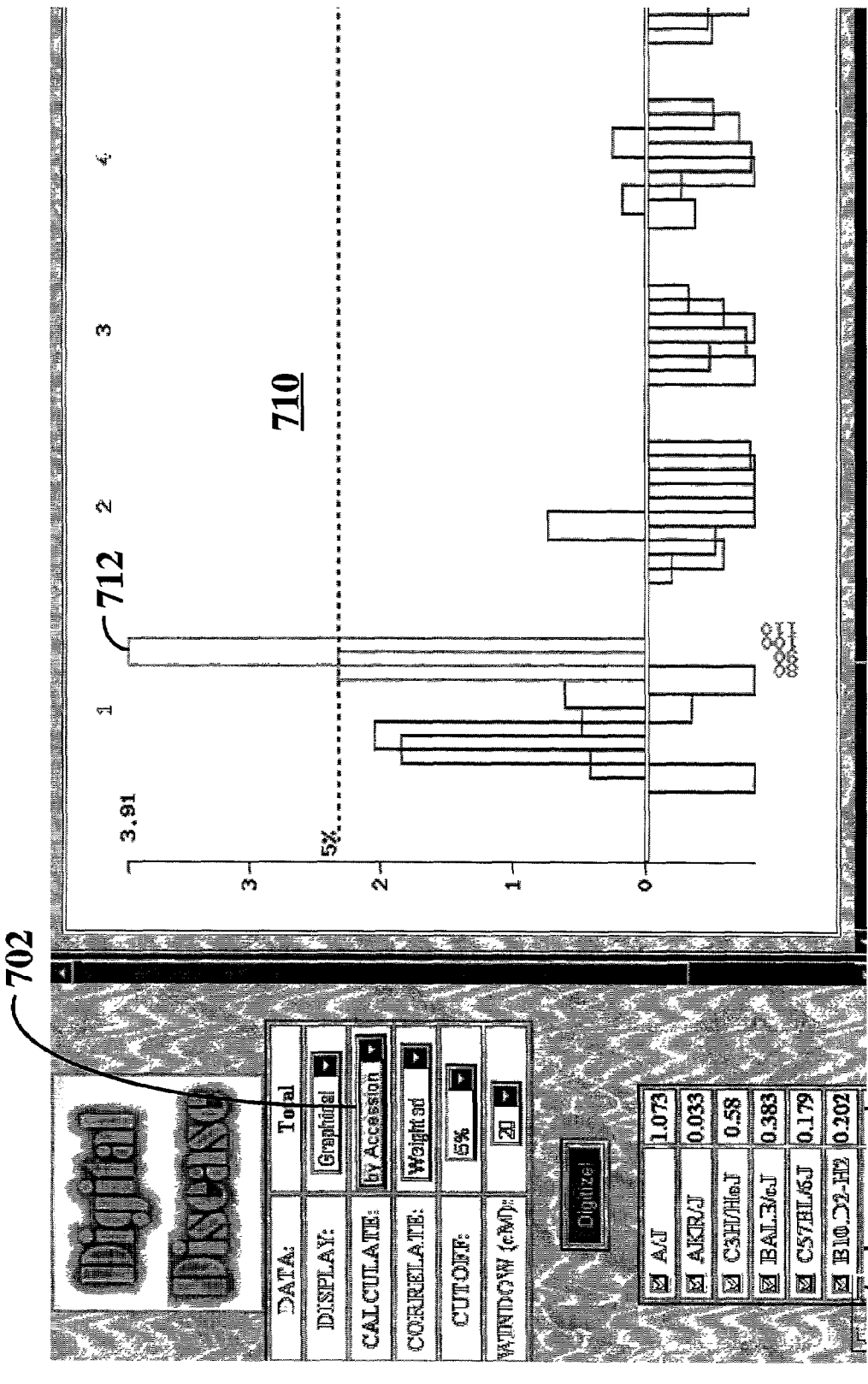
FIG. 7 illustrates a graphical user interface having a toggle that is set to a mode in which each accession number in a locus L contributes equally to a corresponding genotypic matrix G.

FIG. 7 illustrates a user interface 700 in which a toggle 702 allows the user to compute genotypic matrices by accession number. That is, each accession number in the locus L selected in processing step 204 (FIG. 2) is given a single "vote" in computing the corresponding genotypic matrix. In FIG. 7 the name of a plurality of different mouse strains is listed in panel 704. Further, for each of the mouse strains, values for a particular phenotype that correspond to the respective mouse strain is shown in panel 706. A panel of check boxes 708 is further provided in user interface 700. The check boxes allow the user to determine which strains will be used in the computations of the present invention. Accordingly, when a strain is not selected using the check box that corresponds to a given strain, the phenotypic data of that strain is not used to compute the phenotypic data structure constructed in processing step 202 (FIG. 2). After computations in accordance with FIG. 2 are run, the correlation coefficient or correlative measure between genotypic data and phenotypic data is plotted in panel 710. In panel 710, the x-axis is chromosome location in the organism of interest. The y-axis is the number of standard deviations that a particular correlation coefficient or correlative measure is above the median correlation coefficient or correlative measure from the set of correlation coefficients or correlative measures computed using the processing steps disclosed in FIG. 2. For instance, peak 712 represents a particular 20 cM window in the genome of a mouse that has a correlation coefficient that is 3.92 standard deviations above the median correlation coefficient. Panel 710 may be considered a correlation map of the genome of the organism under study.

Figure 8:
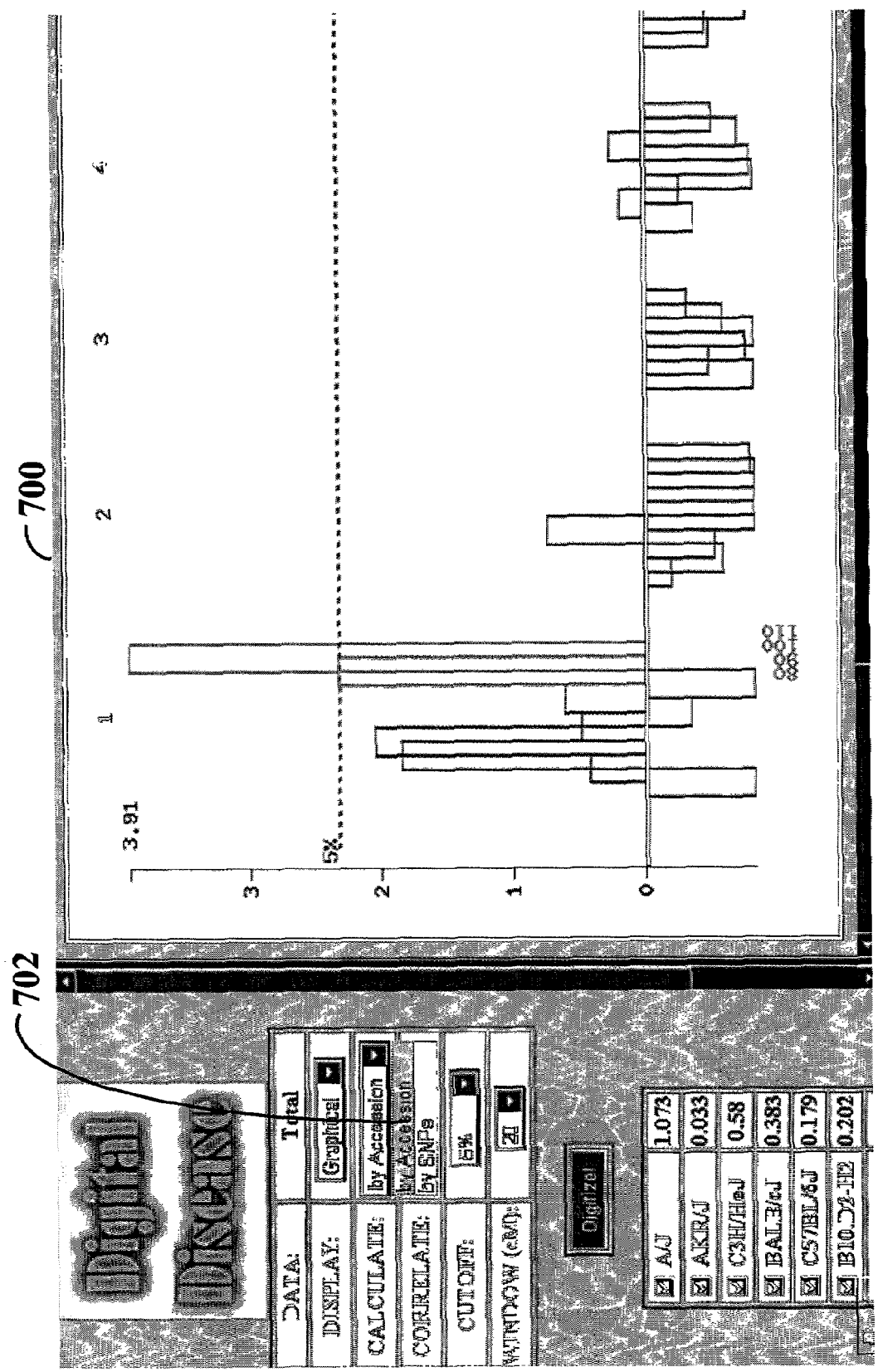
FIG. 8 illustrates a graphical user interface in which a toggle is used to toggle between a mode in which each locus position x contributes equally to a corresponding genotypic matrix ("by SNP") and a mode in which each accession number contributes to a corresponding genotypic matrix.
Figure 9:
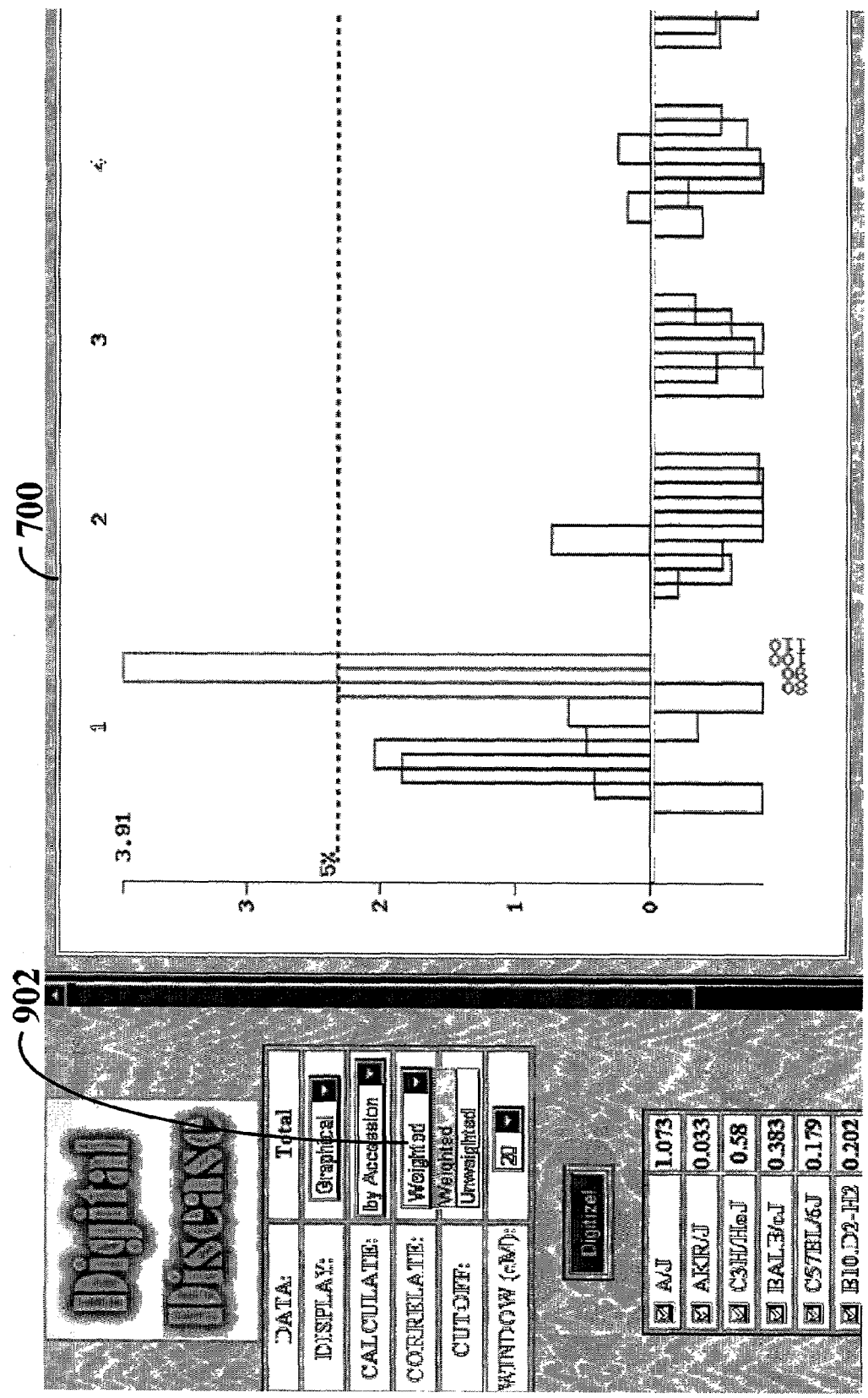
FIG. 9 illustrates a graphical user interface in which a toggle is provided for switching between a weighted mode, in which each computed correlative measure is weighted by the number of locus positions x that are represented by a correlative measure, and an unweighted mode, in which each computed correlation coefficient is not weighted by the number of locus positions x within the respective locus L.
Figure 10:
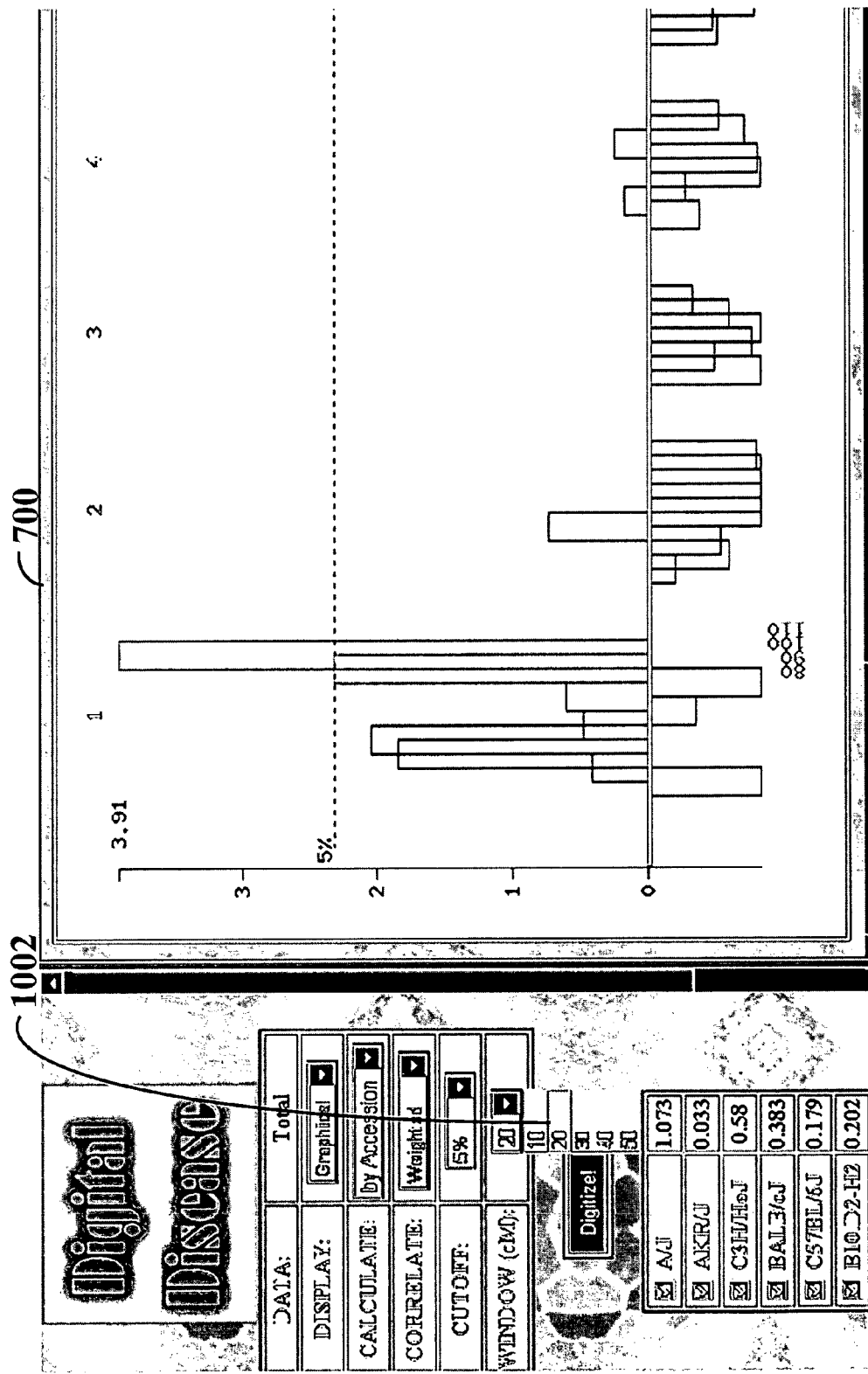
FIG. 10 illustrates a graphical user interface in which a user toggle is provided for allowing a user to determine the size of the locus L that is used in various computations in accordance with one embodiment of the present invention.

FIG. 8. illustrates the same user interface 700 illustrated in FIG. 7. However, in FIG. 8, toggle 702 is set so that genotypic matrices are computed by individual SNPs. Thus, in the setting shown in FIG. 8, genotypic matrices are computed in an unweighted fashion, where each SNP gets one "vote" in computing the genotypic matrix.

Some embodiments of the present invention provide a user toggle 902 (FIG. 9) that allows the user to switch between unweighted and weighted modes. When in weighted mode, correlative measures are computed in instances of processing step 208 (FIG. 2). Each correlative measure is weighted by the number of locus positions x within locus L that is represented by the correlative measure. When in unweighted mode, a correlation coefficient is computed in processing step 208 using an algorithm such as linear regression. When in unweighted mode, correlation coefficients computed in instances of processing step 208 (FIG. 2) are not weighted by the number of locus positions x within the locus L that are represented by the correlation coefficient.

Some embodiments of the present invention provide a user toggle 1002 (FIG. 10) that allows the user to set a window size. This window size is used to determine the size of the locus L that is selected in successive instances of processing step 204 (FIG. 2). In one embodiment, window size is measured in centiMorgans. However, it will be appreciated that other units of measure, such as number of nucleotide bases, kilobases, or megabases, are possible.

EXAMPLES

Building a murine SNP database. The methods of the present invention are particularly useful in embodiments that make use of genetic information from inbred strains of an organism of interest. Thus, a genotypic database 52 was developed that contains allele information across 15 inbred strains. At Roche Bioscience, 293 SNPs at defined locations were identified in the mouse genome. The SNPs were identified by direct sequencing of PCR amplification products from defined chromosomal locations. This database also incorporates published allele information for 2848 SNPs, 45% of which are characterized in a subset of *M. Musculus* strains, and 55% of the SNPs are polymorphic between *M. castaneus* and one or more *M. musculus* subspecies (Lindblad-Toh, et al., Nature Genetics April; 24, 381-386, 2000). User queries regarding SNPs found within a specified chromosomal region or between selected inbred strains are executed in real time and provided via user interface 24 (FIG. 1).

Example 1

Figure 3:
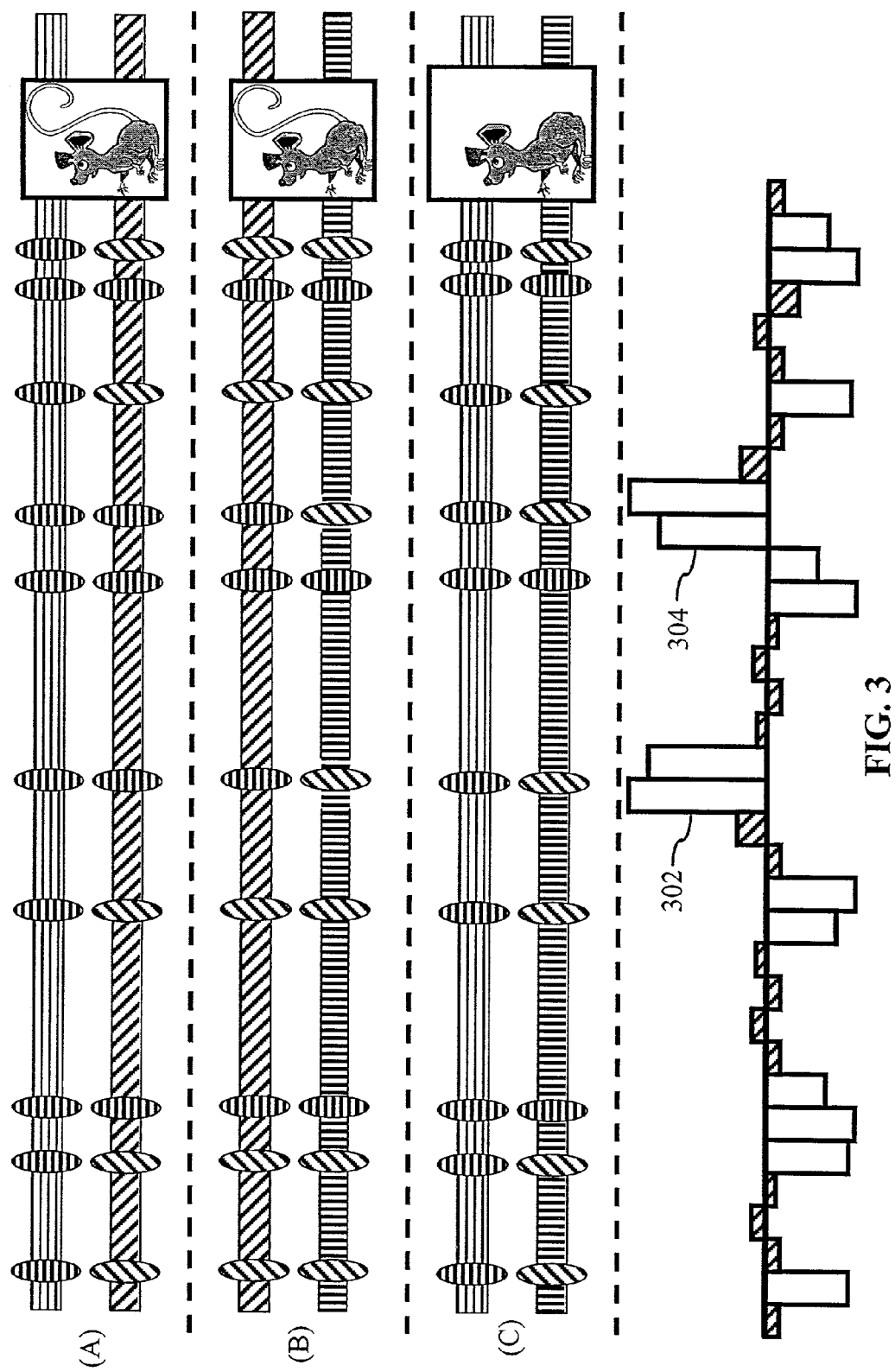
FIG. 3 illustrates a hypothetical representation of the method for computational prediction of QTL intervals in accordance with one embodiment of the present invention.

Hypothetical example of the method for prediction of QTL regions. To aid in the understanding of the methods of the present invention, FIG. 3 is provided. FIG. 3 shows hypothetical comparisons, in accordance with the methods of the present invention, between three mouse strains (A, B, C) using SNP information found in the murine SNP database. Each of the two chromosomes sets for a given mouse strain is represented by a horizontal box along the horizontal axis of FIG. 3. Each chromosome set is characterized by the hatching type (horizontal, diagonal, and vertical). Chromosomes with the same hatching style in each of the mouse strains are identical. Cross hatched or diagonally hatched ovals respectively represent alleles at specific chromosomal positions. A dashed horizontal line is used to differentiate each of the mouse strains and the accompanying chart at the bottom of FIG. 3.

In the hypothetical example provided in FIG. 3, two of the three strains, (A) and (B), exhibit a similar phenotype. That is, strains A and B exhibit a similar phenotype (full size tail), while strain C has a different phenotype (short tail). SNP alleles at particular chromosomal regions are represented as cross hatched or diagonally hatched ovals. A series of pairwise comparisons, in accordance with the algorithm illustrated in FIG. 2, are made to establish the correlation value between the phenotype and genotype for each locus. In each of these series of pairwise comparisons, allelic differences in a respective segment of the chromosome of each of the mouse strains is correlated with the phenotypic difference between each mouse strain. Graphic analysis of the correlation data between the respective strains is shown at the bottom of FIG. 3. The analysis indicates that while most sites exhibit a negative correlation with respect to murine tail length, two chromosomal regions (302) and (304) have a strong positive correlation. In fact, 302 and 304 are the chromosomal regions predicted to have genes regulating tail length.

The following four examples, (Examples 2 through 5) are made with reference to FIG. 4. FIG. 4 illustrates the correlation between the genotype and phenotype distributions for all 19 mouse autosomal chromosomes for a given trait. Loci are arranged proximal to distal for each chromosome. Each bar represents a 30 cM interval of the respective chromosome and neighboring bars are offset by 10 cM. Dotted line 402 represents a useful cutoff for analyzing the data, with the highest correlated ten percent of the genome being above this line.

Example 2

Predicting the chromosomal location of the MHC complex. The methods of the present invention were used to predict the chromosomal location of the MHC complex, which has been mapped to murine chromosome 17, using the H2 haplotypes for the MHC K locus for 10 inbred strains (Anonymous, JAX Notes 475, 1998). Phenotypic distances for strains that shared a haplotype were set to zero, and a distance of one was used for strains of different haplotypes. The SNPs within and near the MHC region had a genotypic distribution which was highly correlated with the phenotypic distances; the correlation value for interval 440 (FIG. 4A) was 5.35 standard deviations above the average for all loci analyzed. There were no other peaks throughout the mouse genome that exhibited a comparable correlation with the phenotype. The computational analysis, executed in accordance with the methods of the present invention, excluded 96% of the mouse genome from consideration without missing the genomic region known to contain the MHC.

Example 3

Identification of the QTLs that correspond to allergic asthma. The chromosomal positions that regulate susceptibility to experimental allergic asthma have been investigated using prior art techniques. For example, published analyses of intercross progeny between susceptible (A/J) and resistant (C3H/HeJ) mouse strains identified QTL intervals on chromosomes 2 and 7 (Ewart, et al., Am J Respir Cell Mol Biol 23, 537-545, 2000; Karp, et al., Nature Immunology 1, 221-226, 2000). The ability of the methods of the present invention to identify these chromosomal regions was investigated.

Figure 4A:
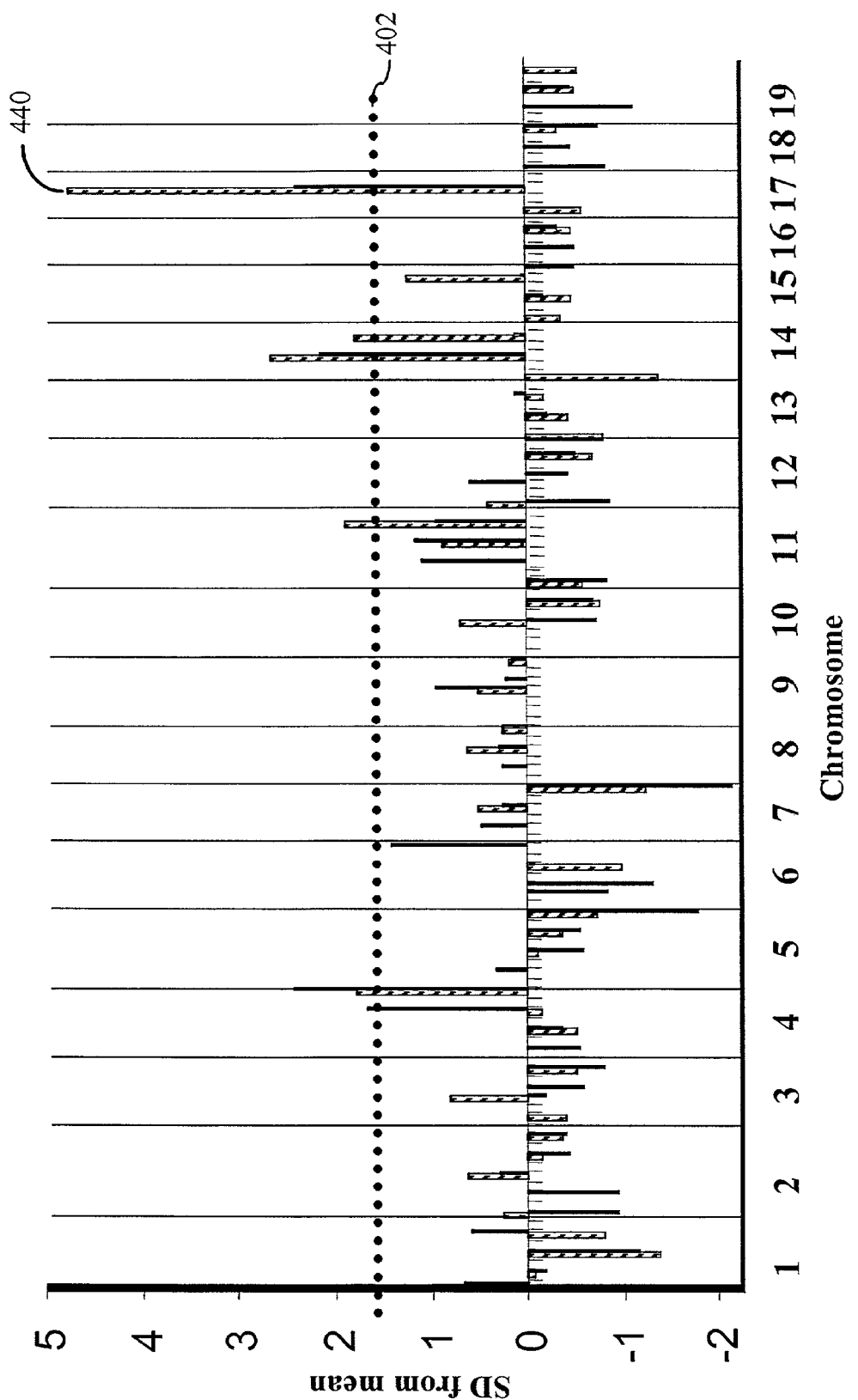
FIGS. 4A-4D illustrate the computational prediction of chromosomal regions containing genes that determine MHC haplotype (FIG. 4A), lymphoma susceptibility (FIG. 4B), airway hyperresponsiveness (FIG. 4C) and retinal ganglion number (FIG. 4D) in accordance with one embodiment of the present invention.
Figure 4B:
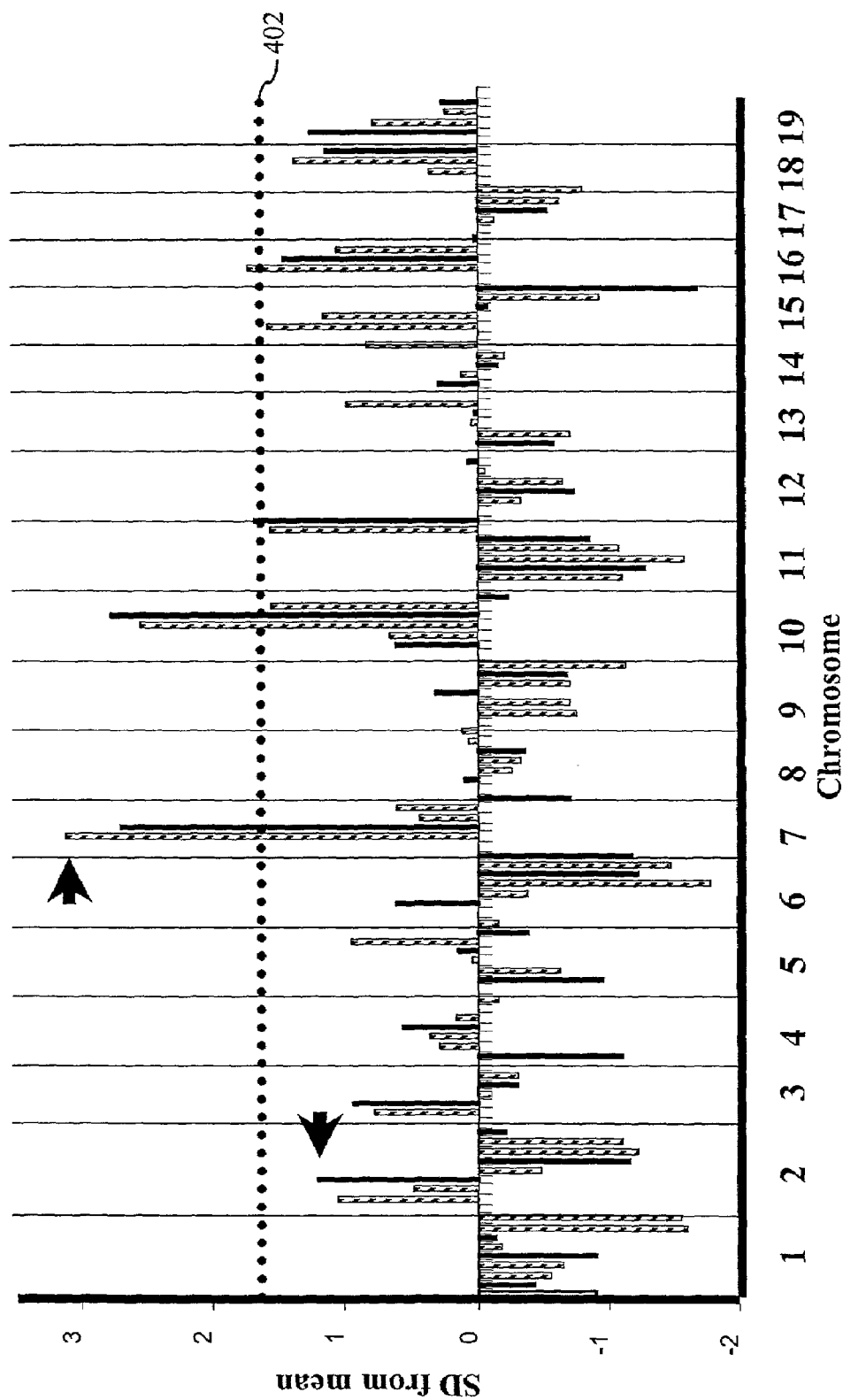

The phenotypic distance used to populate the phenotypic matrix was the absolute difference between the measured airway response after allergen-challenge for each strain pair. The experimentally identified QTL intervals on chromosomes 2 and 7 were among the strongest peaks identified by the methods of the present invention (FIG. 4B). The computational method excluded 80% of the mouse genome from consideration without missing the experimentally mapped QTL regions using airway responsiveness data from only 5 inbred mouse strains.

Example 4

Figure 4C:
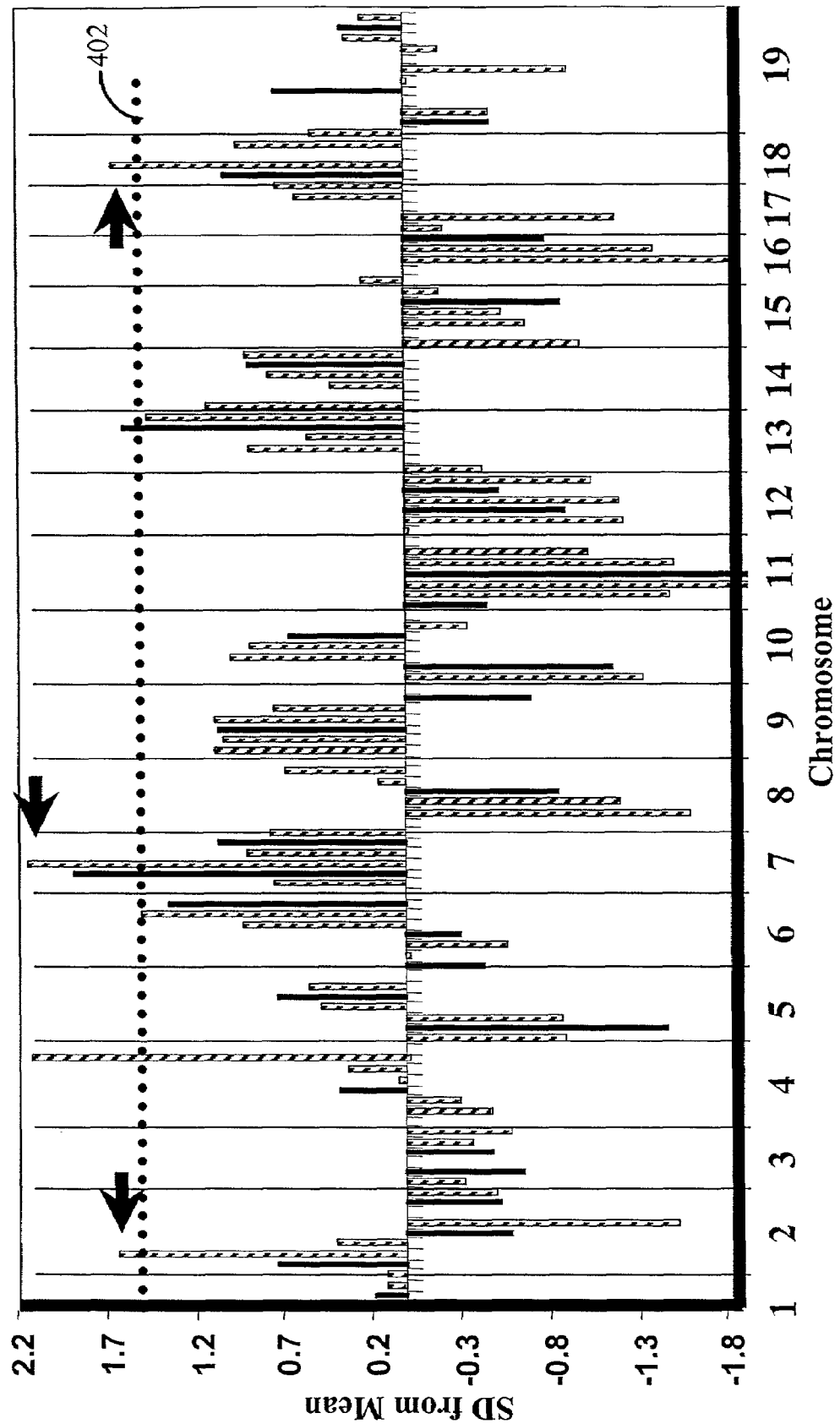

Lifespan data. Lifespan data for five mouse strains, which reflected susceptibility to T cell lymphoma, has been published (Chrisp et al., Veterinary Pathology 33, 735-743, 1996). Using conventional techniques, three susceptibility regions were experimentally identified by analysis of intercross progeny (Wielowieyski et al., Mammalian Genome 10, 623-627, 1999; Gilbert, et al., J. Virol. 67, 2083-2090, 1993; Mucenski et al., Molecular & Cellular Biology 6, 4236-4243, 1986; Mucenski et al, Molecular & Cellular Biology 8, 301-308, 1988); and all three regions were predicted by the computational genome scan (FIG. 4C). In this example, over ninety percent of the genome could be excluded from consideration by the computational method without overlooking any experimentally verified QTL interval.

Example 5

Figure 4D:
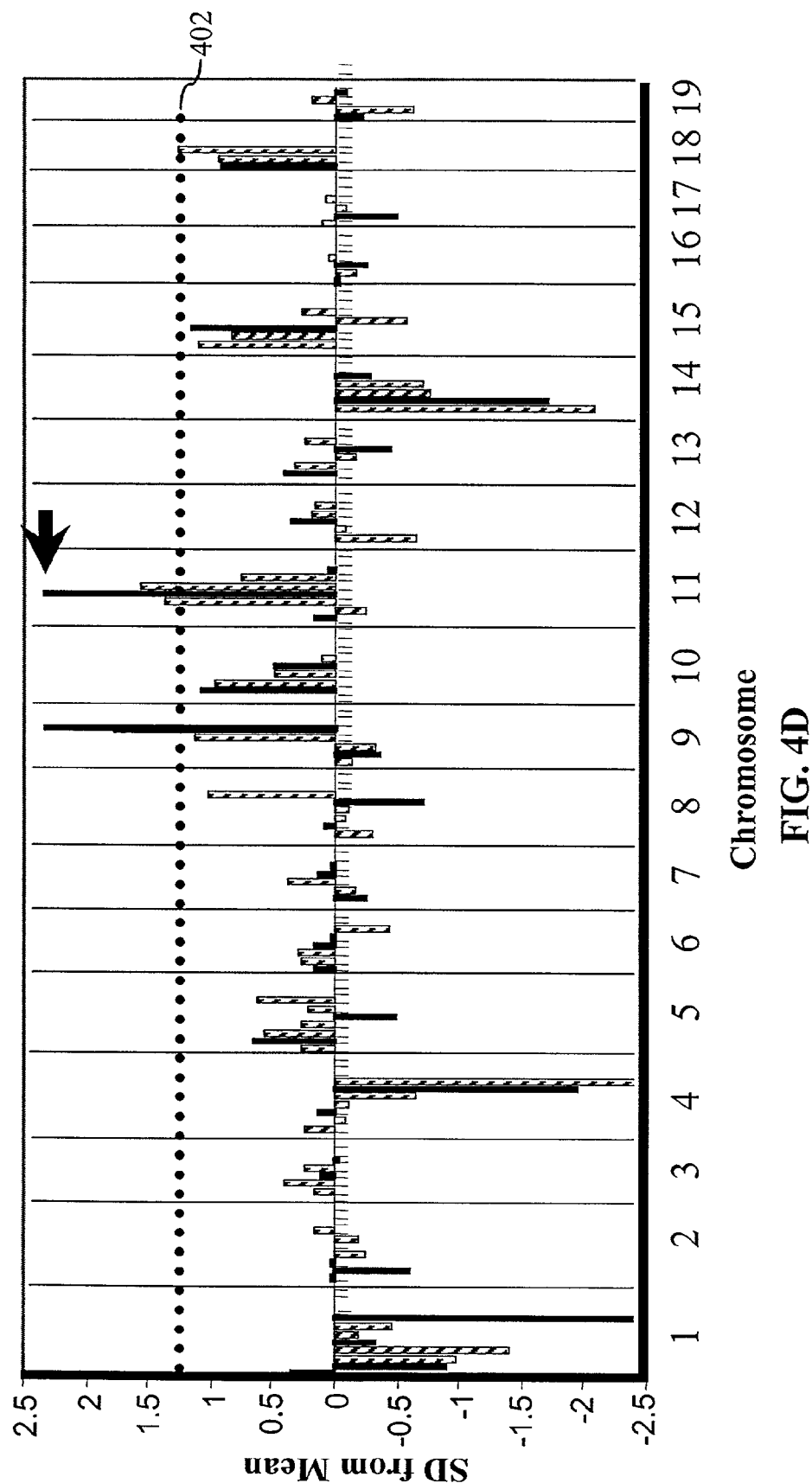

Retinal ganglion cells. In another example, the measured density of retinal ganglion cells was used as a phenotype. Using conventional techniques, the QTLs associated with this phenotype have been localized to chromosome 11 in the mouse genome (Williams et al., Journal of Neuroscience 18, 138-146, 1998). The experimentally verified QTL interval on chromosome 11 was contained in the chromosomal regions predicted by the methods of the present invention, while 96% of the mouse genome was excluded (FIG. 4D).

Example 6

Additional phenotypic traits. The ability of the computational method of the present invention to identify candidate chromosomal regions that are associated with six additional quantitative traits was performed. The chromosomal positions for these six additional quantitative traits are derived from published studies that provided mapped locus positions (quantitative trait loci; QTLs) as well as phenotypic data across multiple inbred strains for each trait (Table 2). As shown in Table 2, a total of 10 QTLs from 6 published phenotypic studies are identified from the literature. Each QTL resides on a different chromosome. Centimorgan positions were interpreted from published marker locations on physical maps.

TABLE 2

Published chromosomal positions of QTLs that have been associated with particular phenotypes using conventional techniques

| Phenotype | Chromosome (cM) | Notes |
|---|---|---|
| AHR | 2 (23.5), 7 (1) | Allergen induced airway response (APTI) |
| Eye weight | 5 (0-10) | Mouse eye weight (grams), day 75 |
| Retinal anglion | 11 (57.5) | Retinal ganglion cell # |
| Lymphoma | 1 (62-73), 6 (30), 16 (50) | Tumor incidence, lifespan |
| MHC | 17 (10) | H2 K serotyping |
| PKC | 11 (66), 3 (16.4, 45) | PKC-α protein amount, activity |

The ability of the methods of the present invention to correctly predict chromosomal regions containing experimentally verified QTL intervals associated with the six phenotypic traits is presented in Table 3.

TABLE 3

Summary of predictions made in accordance with the methods of the present invention

| Phenotype | Experimentally Verified | Methods of the Present Invention | | |
|---|---|---|---|---|
| | | Correct | Predicted | Threshold (%) |
| AHR | 2 | 2 | 8 | 19 |
| Eye weight | 1 | 1 | 6 | 17 |
| Ganglion | 1 | 1 | 2 | 4 |
| Lymphoma | 3 | 3 | 4 | 8 |
| MHC | 1 | 1 | 1 | 2 |
| PKC | 2 | 2 | 6 | 2, 11 |
| Totals | 10 | 10 | 27 | |

As shown in Table 3, the methods of the present invention identified all ten experimentally characterized QTL intervals. In addition, seventeen other chromosomal regions were predicted by this computational method. Whether these predicted regions affect phenotypic traits has not yet been experimentally verified. The threshold required for correct identification of a QTL varied from two percent to nineteen percent of the complete mouse genome.

Figure 5:
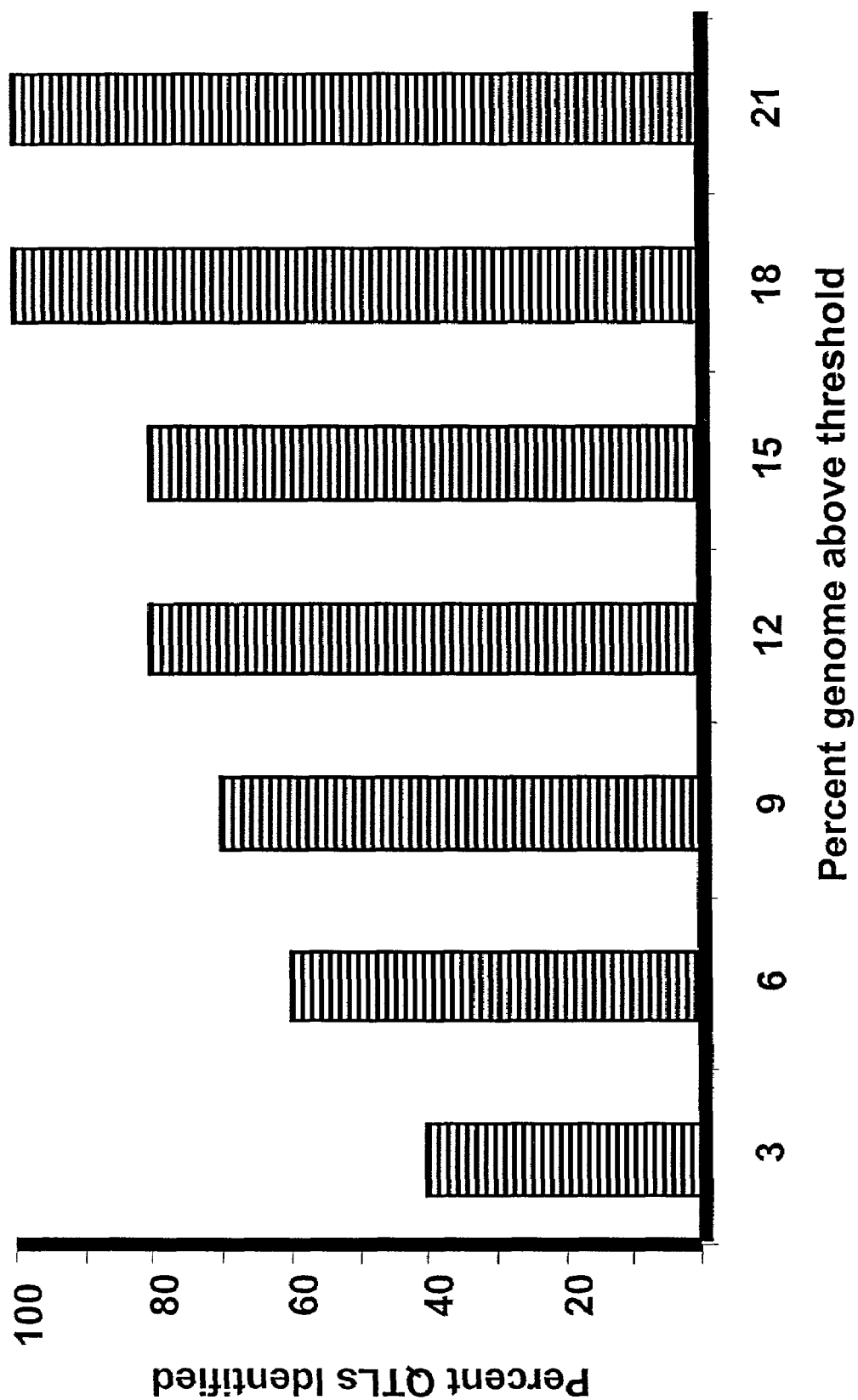
FIG. 5 illustrates an analysis of the sensitivity of the computational genome scanning method for prediction using ten experimentally verified QTL intervals. A graph of the percentage of correct predictions as a function of the amount of genomic sequence (percent) contained within the predicted regions is plotted.

The percentage of correct predictions as a function of the percentage of the mouse genome contained within the predicted chromosomal regions was examined. If predicted regions contained eighteen percent of the mouse genome (by selecting eighteen percent of the peaks with the highest correlation), all ten experimentally verified QTL intervals were correctly identified (FIG. 5). As the threshold was raised, limiting the number of predicted candidate chromosomal regions, the methods of the present invention missed some experimentally verified QTL intervals for these traits. When only three (or nine) percent of the genome was above the threshold, the method identified four (or seven) of the ten verified QTL intervals for these traits (FIG. 5).

When a genome-wide threshold of ten percent was used, the genomic region to search for candidate genes was computationally reduced by an order of magnitude. Since the average size of a predicted genomic region was 38 cM, the 1500 cM mouse genome could be subdivided into approximately forty regions. The computational method was used for seven different phenotypes, so approximately 280 genomic intervals (38-cM in size) were examined. This method correctly identified seven of ten experimentally validated QTL intervals, while missing three, at the ten percent genome-wide threshold. The algorithm further predicted 23 genomic intervals were involved in a phenotypic trait where no QTL had been experimentally characterized. Finally, the computational method and experimental analysis agreed on 240 loci that were not QTL intervals for the phenotypes examined. This data can be assembled into a 2×2 matrix to assess the ability of the computational method to predict QTL intervals. A Fisher Exact test yields a highly significant P value ($7.0 \times 10^{-6}$) for the computationally predicted intervals.

In summary, the methods of the present invention were able to identify ten QTLs for seven phenotypic traits that had been previously identified by prior art techniques. Each of the experimentally verified QTL intervals was identified by the methods of the present invention. The genotypic array used to identify these chromosomal regions was derived from a murine SNP genotypic database. In each case, the conventionally identified QTL interval exhibited a computational SNP distribution that was highly correlated with the tested phenotype. The correlation was well above the mean value for the entire genome, and nine of ten were greater than a full standard deviation above the mean.

Example 7

Use of alternative genotypic databases 52. Although the examples provided herein utilize a genotypic database of 15 inbred mouse strains, other types of genotypic databases may be used. For example, suitable genotypic databases include various databases that have various types of gene expression data from platform types such as spotted microarray (microarray), high-density oligonucleotide array (HDA), hybridization filter (filter) and serial analysis of gene expression (SAGE) data.

As a proof of concept, 315 microsatellite polymorphisms were downloaded from the Center for Inherited Disease Research URL http://www.cidrjhmi.edu/download/CIDR_mouse.xls Genotypic database 52 was populated in manner analogous to the case when SNP data was used to populate database 52: if the polymorphisms matched between two mouse strains, a "0" was entered, if they differed, a "1" was entered. In this way, the number of differences between mouse strains was counted for a given locus. The remainder of the analysis was performed in accordance with the methods of the present invention. For this trial, the MHC locus was identified on chromosome 17. Although the QTL for the MHC region was not as clearly distinguished when using microsatellite information as it was for SNP data, it should be noted that the microsatellite data used for the trial was sparser than the information currently available in the mouse SNP database.

Example 8

Figure 6:
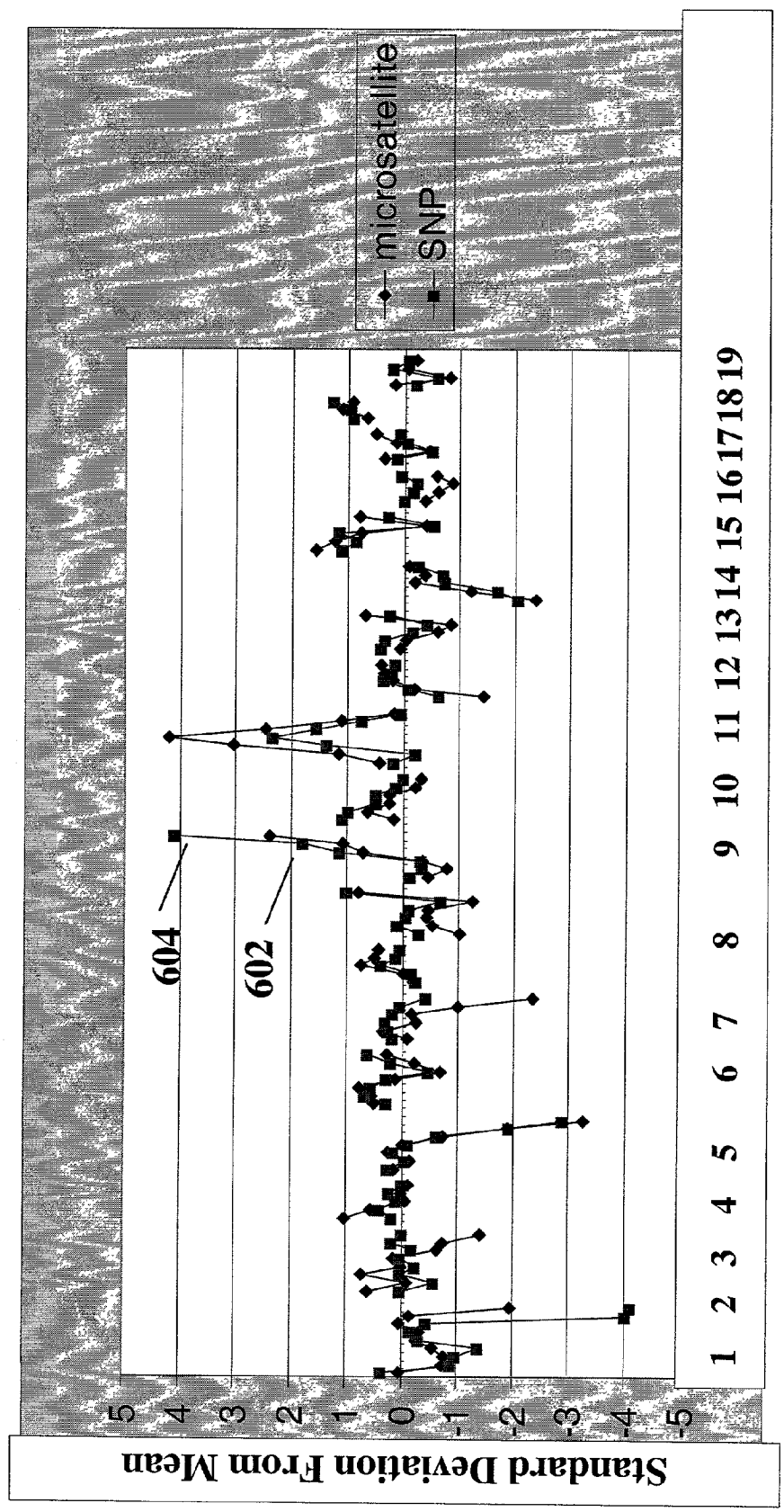
FIG. 6 illustrates the comparison of a genotypic database 52 that includes SNP data versus a genotypic database that includes microsatellite data in identifying the murine chromosomal location for the phenotypic trait of retinal ganglion cell formation, in accordance with one embodiment of the present invention.

Comparison of the performance of a genotypic database 52 populated with SNP data to a genotypic database 52 populated with microsatellite data. The genotypic database 52 populated with microsatellite data as described in Example 7 was compared to the previously described genotypic database 52 that contains allele information across 15 inbred strains for 287 SNPs at defined locations in the mouse genome. In this case, the phenotype is the formation of retinal ganglion cells in infant mice. The experimentally verified QTL that correlates with this phenotype is on chromosome 11. As illustrated in FIG. 6, the genotypic database 52 populated with the microsatellite information more strongly identifies the correct QTL peak than the genotypic database 52 populated with SNP data (4.2 standard deviations with microsatellites versus 2.3 standard deviations with SNPs). Furthermore, the results using the microsatellite data are less noisy than the results using the SNP data. See, for example, the reduced positive peak on chromosome 9 using the microsatellite data (602 versus 604).

Example 9

Use of Perturbations. The present invention may be used to correlate phenotypes of a plurality of strains of a biological sample with specific positions in the genome of the biological sample before and after the biological sample has been exposed to a perturbation. In this approach, two sets of experiments are performed. In the first set, the methods of the present invention are used to correlate genotypes to phenotypes before the plurality of strains of the biological sample are exposed to a perturbation. In the second set of experiments, the plurality of strains of the biological samples are each exposed to a perturbation and the methods of the present invention are used to correlate genotypes to phenotypes. Then, the correlations computed in the first set of experiments are compared to the correlations computed in the second set of experiments. By comparing differences or similarities between these two sets of correlations, it is possible to identify regions of the genome of the biological sample that are highly responsive to the perturbation. In one embodiment of the present invention, the biological sample is a mouse or rat.

One embodiment of the present invention provides a method of determining a portion of a genome of an organism that is responsive to a perturbation. In the method, a first phenotypic data structure that represents a difference in a first phenotype between different strains of said organism is produced. The genome of the organism includes a plurality of loci. The first phenotype is measured for each of the different strains of the organism when each of these different strains is in a first state. Next, a genotypic data structure is established. The genotypic data structure corresponds to a locus selected from the plurality of loci. Further, the genotypic data structure represents a variation of at least one component of the locus between different strains of the organism. The first phenotypic data structure is compared to the genotypic data structure to form a correlation value. These establishing and comparing steps are repeated for each locus in the plurality of loci, thereby identifying a first set of genotypic data structures that form a high correlation value relative to all other genotypic data structures that are compared to the first phenotypic data structure during the comparing step.

The method proceeds with the computation of the second phenotypic data structure that represents a difference in a second phenotype between different strains of the organism. The second phenotype is measured for each of the different strains of the organism when each of the different strain is in a second state. This second state is produced by exposing each strain of the organism to a perturbation.

Next, the second phenotypic data structure is correlated to the genotypic data structure to form a correlation value. The computing and correlating steps are repeated for each locus in the plurality of loci, thereby identifying a second set of genotypic data structures that form a high correlation value relative to all other genotypic data structures that are compared to the second phenotypic data structure during the correlating step. Finally, a dissimilarity in the first set of genotypic data structures and the second set of genotypic structures is resolved, thereby determining the portion of the genome of the organism that is responsive to the perturbation.

The phenotypes selected for study in the two sets of experiments may be any type of phenotype that is reliably measured. Thus, a phenotype may be, for example, life-span of the biological sample, the basal serum level of an antibody in the blood of the biological sample, the serum level of an antibody in the blood of the biological sample after exposure of the biological sample to a perturbation, the response of a biological sample in one of the various pain models described in Example 10 after the biological sample has been exposed to a pain relieving drug, etc. Many other phenotypes are possible and all such phenotypes are within the scope of the present invention.

The term "perturbation" within the context of this example is broad. A perturbation can be the exposure of a biological sample to a chemical compound such as a pharmacological or carcinogenic agent, the addition of an exogenous gene into the genome, or the removal of an exogenous gene. Thus, for example, the antibody serum level in mice representing a plurality of difference mice species can be measured before and after exposing each strain of mice to an antigen. Then, the genotypic differences in the plurality of different mouse strains is correlated with observed phenotypes before and after exposure of the mice to a perturbation. By comparing the peaks found in the correlation map of the mice before and after exposure to the perturbation, it is possible to localize regions of the mouse genome that are most affected by the perturbation.

The panel of check boxes 708, provided in user interface 700 (FIG. 7), is particularly useful in cases where perturbations are used. For any given perturbation, there will typically be a strain having a phenotype that is more responsive to the perturbation than all other strains studied. To determine how the highly responsive strain affects the correlation map plotted in panel 710 of FIG. 7, one simply deselects the unresponsive species and reruns the calculations.

Once the regions of the genome that are highly responsive to the perturbation have been identified, gene chip expression libraries that include the identified portion of the genome may be examined. Of particular interest is the identification of differential expression of genes in (i) a gene chip library made from a strain of the biological sample before insult with a perturbation and (ii) a gene chip library made from the strain of the biological sample after insult with a perturbation. As is well known in the art, the gene chip library may be a collection of mRNA expression levels or some other metric, such as protein expression levels of individual genes within the organism. Comparison of the differential expression level of genes in the two gene chip libraries leads to the identification of individual genes that exhibit a high degree of differential expression before and after exposure of the biological sample to a perturbation. Correlation of the positions of these individual genes with the regions of the genome identified using the correlation metrics disclosed above provides a method of identifying specific genes that are highly responsive to a perturbation.

Exemplary gene chip expression libraries have been used in studies such as those disclosed in Karp et al. "Identification of complement factor 5 as a susceptibility locus for experimental allergic asthma," Nature Immunology 1(3), 221-226 (2000) and Rozzo et al. "Evidence for an Interferon-inducible Gene, Ifi202, in the Susceptibility of Systemic Lupus," Immunity 15, 435-443 (2001). Furthermore, methods for making several different types of gene chip libraries are provided by vendors such as Hyseq (Sunnyvale California) and Affymax (Palo Alto, Calif.).

Example 10

The following protocols illustrate some of the many ways in which phenotypic data can be derived for biological samples of interest, in order to practice the methods of the present invention.

1. In Vivo Activity in Rats.

The following protocols are generally as described in Faden, 1989, Brain Research 486:228-235 and McIntosh et al., 1989, Neuroscience 28(1):233-244.

1.1 Animals used. Male Sprague-Dawley rats (375-425 g) are obtained from Harlan (Frederick, Md.) and housed for at least 1 week prior to any procedures. The animals are maintained at a constant temperature ($22\pm2°$ C.) and a 12 hr light/dark cycle, with lights on at 6 am and all neurological scoring performed during the light cycle. Food and water are available ad libitum.

1.2 Fluid-Percussion Induced Traumatic Brain Injury (TBI). Rats are anesthetized with sodium pentobarbital (70 mg/kg i.p.), intubated, and implanted with femoral venous and arterial catheters. Brain temperature are assessed indirectly through a thermister in the temporalis muscle. Body temperature is maintained through a feedback-controlled heating blanket. Blood pressure is continuously monitored, and arterial blood gases analyzed periodically. After the animal is placed in a stereotaxic frame, the scalp and temporal muscle are reflected, and a small craniotomy (5 mm) located midway between the lambda and bregma sutures over the left parietal cortex allows insertion of a Leur-Loc that is cemented in place. The fluid-percussion head injury device, manufactured by the Medical College of Virginia, consists of a plexiglass cylindrical reservoir filled with isotonic saline; one end includes a transducer that is mounted and connected to a 5 mm tube that attaches through a male Leur-Loc fitting to the female Leur-Loc cemented at the time of surgery. A pendulum strikes a piston at the opposite end of the device, producing a pressure pulse of approximately 22 msec duration, leading to deformation of underlying brain. The degree of injury is related to the pressure pulse, expressed in atmospheres (atm): 2.6 atm in our laboratory produces a moderate injury with regard to neurological and histological deficit. Sham (control) animals undergo anesthesia and surgery without fluid percussion brain injury.

1.3 Neurological Scoring. Standardized motor scoring is performed at 1, 7 and 14 days after TBI, by individuals unaware of treatment. Motor function is evaluated utilizing three separate tests, each of which is scored via an ordinal scale ranging from 0=severely impaired to 5=normal function. Tests include ability to maintain position on an inclined plane in the vertical and two horizontal positions for 5 sec; forelimb flexion (suspension by the tail) and forced lateral pulsion. Each of seven individual scores (vertical angle, right and left horizontal angle, right and left forelimb flexion, right and left lateral pulsion) are added to yield a composite neurological score ranging from 0 to 35. This scoring method shows high interrater reliability and is very sensitive to pharmacological manipulations (see, Faden et al., 1989, Science 244:798-800).

1.4 Automatic and Analeptic Assessment. Additional groups of uninjured rats are tested for autonomic and analeptic responses immediately prior to and up to 60 minutes following drug administration. For the analeptic study, rats are first anesthetized with 40 mg/kg i.p. sodium pentabarbitone and placed onto an unheated pad on the laboratory bechtop at room temperature ($22\pm2°$ C.). A thermister probe is placed in the rectum to measure core body temperature. After a ten minute period, rats are administered vehicle or drug as described below via the tail vein. Time to recovery of the righting reflex was subsequently determined while temperature is recorded at five minute intervals for all animals.

To assess autonomic responses to perturbations, such as pain relieving drugs, a separate group of rats are anesthesized with 4% isoflurane (1.5 L/min). Catheters are then placed into the right artoid artery and right jugular vein and exteriorized at the back of the neck. Rats are separated one per cage and allowed to recover from anesthesia. The exteriorized catheters are suspended above the rat to prevent biting. Mean arteriolar blood pressure (MAP) is continuously recorded via a transducer connected directly to the arterial catheter for the duration of the study. At 1 h following catheter placement, each rat is administered vehicle or drug via the catheter in the jugular vein as described below.

1.5 Administration of Compounds. Rats are injected via the femoral vein catheter with a single bolus dose (1 mg/kg) with various compounds of interest. The investigator is blinded to drug treatment both at the time of surgery and for neurological scoring. For autonomic and analytic studies, rats are given either normal saline or a compound under study at the times indicated above.

1.6 Data Analysis. Continuous variables compared across groups are examined using an analysis of variance (ANOVA) followed by Bonferroni correction (rightin reflex). Continuous variables subjected to repeated measurements over a period of time (cardiovascular and core temperature measurements) are analyzed using a repeated measurements ANOVA followed by Tukey's pairwise comparison at each time point. Ordinal measurements (composite neurological scores) are evaluated using the non-parametric Kruskal-Wallis ANOVA with individual, non-parametric Mann-Whitney U-tests. Survival differences are compared using the Chi-Square test. A p value <0.05 is considered statistically significant.

2. In Vivo Studies in Mice 2.1 Animals. Male C57B1/6 mice (20-25 g) are obtained from Taconic Farms (Germantown, N.Y.) and housed in an area directly adjoining surgical and behavioral rooms for at least 1 week prior to any procedures. All mice are maintained at a constant temperature ($22\pm2°$ C.) and a 12 hr light/dark cycle, with lights on at 6 am and all behavioral testing performed during the light cycle. Food and water are available ad libitum.

2.2 Controlled Cortical Impact Device. The injury device consists of a microprocessor-controlled pneumatic impactor with a 3.5 mm diameter tip. The impactor is vertically mounted on a mill table (Sherline, USA) which allows for precise adjustment in the vertical plane above the mouse head, which itself is secured to a stereotaxic apparatus (David Kopf Instruments, Calif.) attached to the instrument. The core rod of a linear voltage differential transducer (LVDT, Serotec, USA) is attached to the lower end of the impactor to allow measurement of velocities between 3.0 and 9.0 m/s. Velocity of the impactor is controlled by fine tuning both positive and negative (back) air pressures. An oscilloscope (Tektronix, USA) records the time/displacement curve produced by the downward force on the LVDT, allowing precise measurement of the impactor velocity.

2.3 Surgery. Surgical anesthesia is induced and maintained with 4% and 2% isoflurane respectively, using a flow rate of 1.0-1.5 l oxygen per minute. Depth of anesthesia is assessed by monitoring respiration rate and palpebral and pedal-withdrawal reflexes. The animal is then placed onto a heated pad and core body temperature is monitored and maintained at 38+/−0.2° C. The head is mounted in a stereotaxic frame and the surgical site clipped and prepared with a series of three Nolvasan scrubs followed by sterile saline rinses. A 10 mm mid-line incision is made over the skull, the skin and fascia reflected, and a 4 mm craniotomy made on the central aspect of the left parietal bone with a tissue punch (Roboz, USA). Great care is taken with the removal of the parietal bone to avoid injury to the underlying dura mater which is continuously bathed in sterile normal saline warmed to 37.5° C. The impounder tip of the pneumatic injury device is cleaned with a pad, soaked in absolute alcohol, positioned to the surface of the exposed dura and automatically withdrawn the 44 mm stroke distance. Following injury at a moderate (6.0 m/s velocity, 1 mm tissue deformation depth) level, the incision is closed with interrupted 6-0 silk sutures, anaesthesia is discontinued and the mouse was placed into a heated cage to maintain normothermia for 45 minutes post-injury. All animals are monitored carefully for at least 4 hours post-surgery and then daily. To minimize variation between animals due to anaesthesia during acute neurological testing, 20 minutes is allowed for surgery and five minutes for suturing for each animal.

2.4 Administration of Compounds. Conscious mice are placed in a mouse restrainer and injected via the lateral tail vein with either normal saline or a compound of interest at 30 minutes following controlled cortical impact injury (CCI). The investigator is blinded to drug treatment both at the time of surgery and for neurological and behavioral scoring.

2.5 Acute and Chronic Neurological Evaluation. Chronic neurological recovery is evaluated for all animals using a beam walking task, a method that is particularly good at discriminating fine motor coordination differences between injured and sham-operated animals. The device consists of a narrow wooden beam 6 mm wide and 120 mm in length that is suspended 300 mm above a 60 mm-thick foam rubber pad. The mouse is placed on one end of the beam and the number of footfaults for the right hindlimb recorded over 50 steps counted in either direction on the beam. A basal level of competence at this task was established before surgery with an acceptance level of <10 faults per 50 steps.

2.6 Spatial Learning Evaluation. The Morris watermaze (Morris, 1984, J. Neurosci. Meth. 22:47-60) is employed to assess spatial learning by training mice to locate a hidden, submerged platform using extramaze visual information. The apparatus consists of a large, white circular pool (900 mm diameter, 500 mm high, water temperature 24±1° C.) with a plexiglass platform 76 mm diameter painted white and submerged 15 mm below the surface of water (225 mm high) that is rendered opaque with the addition of dilute, white, non-toxic paint. During training, the platform is hidden in one quadrant 14 cm from the side wall. The mouse is gently placed into the water facing the wall at one of four randomly-chosen locations separated by 90 degrees. The latency to find the hidden platform within a 90 second criterion time is recorded by a blinded observer. On the first trial, mice failing to find the platform within 90 seconds are assisted to the platform. Animals are allowed to remain on the platform for 15 seconds on the first trial and 10 seconds on all subsequent trials. There is an inter-trial interval of 30 minutes, during which time the mice are towel-dried and placed under a heat lamp. A series of 16 training trials administered in blocks of 4 are typically conducted on days 7, 8, 9, and 10-post-surgery.

Example 11

Figure 11:
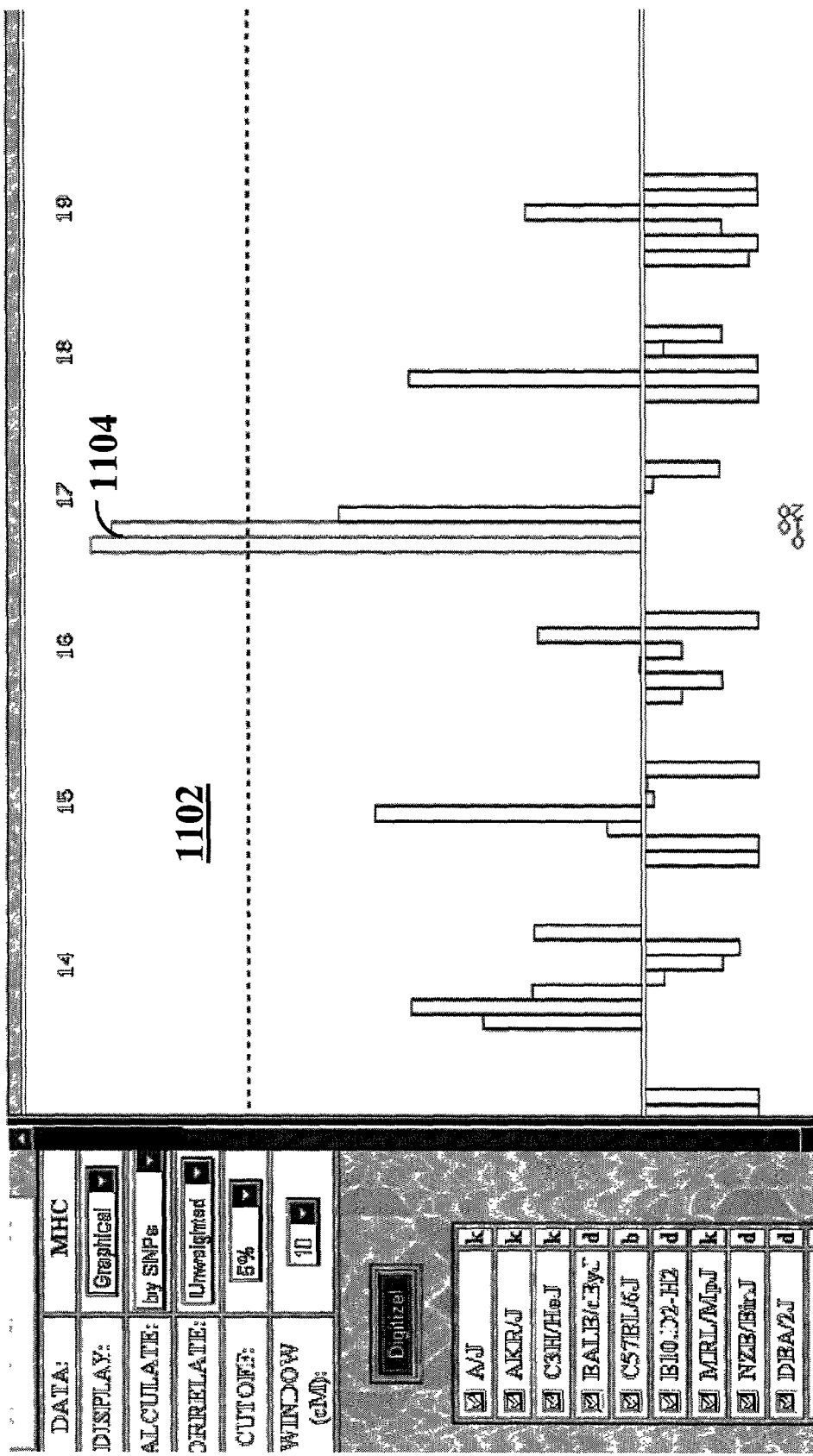
FIG. 11 shows a correlation map where each variation in each locus used to compute the correlation map is allowed to fully contribute to the corresponding genotypic matrix irrespective of whether multiple variations exists in a single gene.

Effect of constraining each gene to a single vote. The advantage of constraining each gene in a locus L to a single vote when constructing a genotypic matrix from component variation matrices S will now be disclosed. FIG. 11 shows a correlation map where each variation in each locus selected in successive instances of processing step 204 is allowed to contribute to the corresponding genotypic matrices irrespective of whether multiple variations exists in a single gene. Thus, in the computation of the correlation map 1102 of FIG. 11, multiple SNPs in the same gene contribute to the corresponding genotypic matrix if they fall within the locus selected in processing step 204 (FIG. 2). The data in panel 1102 is a plot of the correlation coefficient computed between respective genotypic and phenotypic arrays across the entire mouse genome. The correlation map shows a peak 1104 that is 2.8 standard deviations above the mean correlation score computed for the entire map. The gene that is known to affect the trait under study in FIG. 11 is actually in chromosome 17 at 15 cM. Thus, the peak in FIG. 11 is in the wrong region of the mouse genome.

Figure 12:
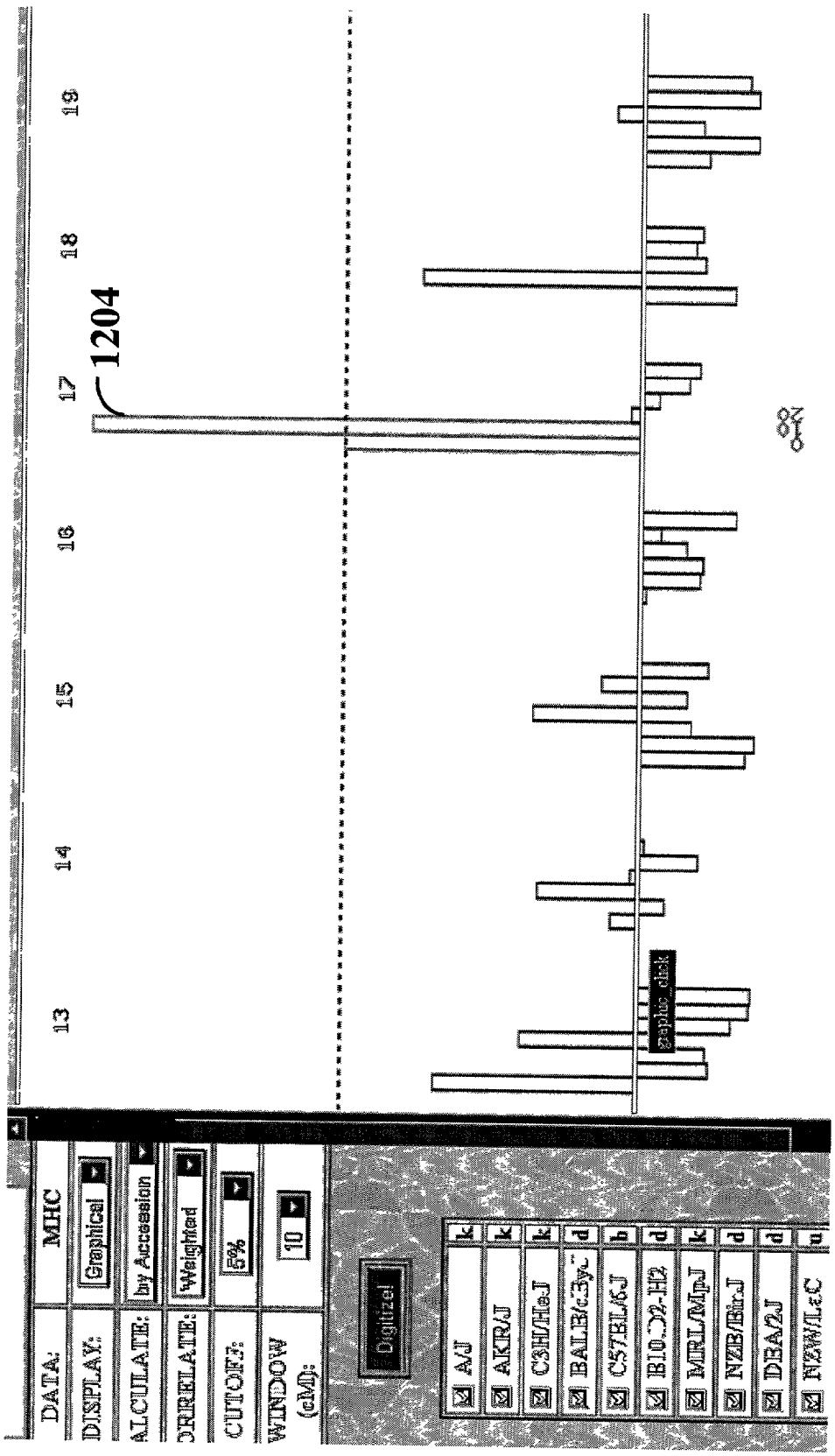
FIG. 12 shows a correlation map where each gene that includes a variation contributes equally to the corresponding genotypic matrix irrespective of the number of variations in each gene.

In FIG. 12, each gene in the locus L selected in processing step 204 is constrained to a single vote in a parliamentary style. Thus, if there are multiple variations in the particular gene, each variation is scaled so that the sum of the variations equals a single vote. When this form of constraint is imposed, the correlation map across the entire mouse genome reveals a peak 1202 that is centered on a gene that is known to influence the trait under study. Furthermore, the peak is now 4.05 standard deviations above the mean score.

DISCUSSION

Computational analysis of genotypic databases 54 using phenotypic data from sources such as inbred parental strains and the methods of the present invention rapidly identifies candidate QTL intervals. This can eliminate many months to years of laboratory work required for generation, characterization and genotyping of intercross progeny. In effect, the methods of the present invention reduce the time required for QTL interval identification from many months to milliseconds.

There are several factors contributing to the successful QTL predictions by computational scanning of the murine SNP genotypic database using the methods of the present invention. The use of inbred mouse strains limits variability due to environment, and timed experimental intervention and sampling limits error in phenotypic assessment. The inbred strains are homozygous at all loci, which eliminates confounding effects due to heterozygosity found in human populations. However, there is no absolute requirement that inbred strains be used to populate genotypic database 52.

The methods of the present invention will greatly accelerate analysis of complex traits and mammalian disease biology. Recently, there has been increased emphasis on using chemical mutagenesis in the mouse as a method for studying complex biology. This has occurred as a result of the difficulties noted by investigators searching for complex trait loci using standard methods for QTL analysis. For a review, see Nadeau and Frankel, Nature Genetics August; 25, 381-384, 2000. However, analysis of genetic variation among existing inbred mouse strains can be markedly accelerated by application of the methods of the present invention. Of course, understanding the genetic basis of complex disease requires additional steps beyond computational prediction of genomic intervals. Specific gene candidates must be identified and evaluated before the underlying mutations can be identified and effective treatment strategies can be designed, tested in animal models, and developed for use with humans.

Example 12

Exemplary computer code. Exemplary computer code from the file "Input_output_dev.pm" corresponding to displays such as shown in FIGS. 7-12:

```
# PRINT THE CUTOFF POPUP MENU
@formerrows = { };
push (@formerrows, th("DATA:") . th(font({
-color=>'yellow'},$global{"data_name"})) );
push (@formerrows, th("DISPLAY:") . th(popup_menu(
-name=>'view',
-value=>['Threshold', 'Interval', 'Graphical'],
-default=>'Graphical')));
push (@formerrows, th("CALCULATE:") . th(popup_
menu(
-name=>'calc_method',
-value=>['by Accession', 'by SNPs'],
-default=>'by Accession')));
push (@formerrows, th("CORRELATE:") . th(popup_
menu(
-name=>'correl_method',
-value=>['Weighted', 'Unweighted'],
-default=>'Weighted')));
push (@formerrows, th("CUTOFF:") . th(popup_menu(
-name=>'cutoff',
-value=>['5%', '10%', '15%', '20%', '25%', '30%',
'40%', '50%', 'NONE'],
-default=>'20%')));
push (@formerrows, th("WINDOW (cM):") . th(popup_
menu(
-name=>'window_size',
-value=>['10', '20', '30', '40', '50'],
-default=>'30')));
print center table ({-border=>'2', -align=>CENTER, -
bgcolor=>'black'}, Tr(\@formerrows)), p, p;
```

Exemplary computer code from the file "Input_output_dev.pm" for displaying the cutoff line that is found in any of FIGS. 7-12:

```
# DRAW PCT CUTOFF LINE
DrawPct_Cut ($closest_pct_value, $im);
$png_data = $im->png;
$global{"timestamp"} = time;
open         (DISPLAY,         ">$image_dir/
   $global{'timestamp'}.png");
binmode DISPLAY;
print DISPLAY $png_data;
close DISPLAY;
}
sub DrawPct_Cut ($closest_pct_value, $im)
{
my $pct = $_[0];
my $image = $_[1];
$image->dashedLine($indent+15, $pct, $length, $pct,
$color{"orange"});
$image->dashedLine($indent+15, $pct, $length, $pct+1,
$color{"orange"});
#$image->dashedLine($indent+15,   $pct+2,   $length,
$pct+2,
$color{"orange"});
$image->string(gdGiantFont, $indent+5, $pct-14,
$global{'cutoff'}, $color{"orange"});
}
```

ALTERNATIVE EMBODIMENTS

The foregoing descriptions of specific embodiments of the present invention are presented for purposes of illustration and description. They are not intended to be exhaustive or to limit the invention to the precise forms disclosed, obviously many modifications and variations are possible in view of the above teachings. For example, the techniques of the invention may be applied using pooled or clustered genetic variation information as a source for the genotypic data structure or genetic variation information from individual samples. Similarly, the phenotypic information provided from sources, such as phenotypic data file 60, may be in the form of pooled or clustered phenotypic data or phenotypic data from individual organisms. Furthermore, genotypic database 52 may represent inbred strains of the organism of interest or randomized strains of the organism of interest that have not been inbred. Because of the overwhelming homology between murine and human genomes, the examples provided herein clearly demonstrate that the methods of the present invention provide an invaluable tool for correlating human phenotypic traits with specific loci in the human genome.

While the examples provided herein describe the comparison of a plurality of genotypic data structures to a phenotypic data structure, one of skill in the art will appreciate that many other types of comparisons may be practiced in accordance with the present invention. For instance, consider the genotypic to phenotypic data structure comparison as a two-dimensional comparison. Higher dimensional comparisons than the two-dimensional comparison are possible. For instance, one embodiment of the present invention provides for a three dimensional comparison of the class: "genotypic data structure" versus "phenotypic data structure one" versus "phenotypic data structure two." Another example of a type of comparison within the scope of the present invention includes a comparison of "SNP genotypic data" to "disease phenotypic data" to "microarray data."

REFERENCES CITED AND CONCLUSION

All references cited herein are incorporated herein by reference in their entirety and for all purposes to the same extent as if each individual publication or patent or patent application was specifically and individually indicated to be incorporated by reference in its entirety for all purposes.

The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the following claims and their equivalents.

We claim:

1. A method of associating a phenotype with one or more candidate chromosomal regions in a genome of a species using a phenotypic data structure that comprises a difference in said phenotype between different strains of said species, said genome including a plurality of loci, said method comprising:

establishing a genotypic data structure using a suitably programmed computer, said genotypic data structure corresponding to a locus in said plurality of loci, said genotypic data structure comprising a variation of at least one component of said locus between different strains of said species;

determining a correlation value for said genotypic data structure by a comparison of said phenotypic data structure with said genotypic data structure using a suitably programmed computer;

repeating said establishing and determining steps for each locus in said plurality of loci using a suitably programmed computer, thereby establishing a plurality of genotypic data structures and, for each respective genotypic data structure in the plurality of genotypic data structures, a correlation value;

identifying one or more genotypic data structures in said plurality of genotypic data structures that have correlation values that are higher than the correlation values for all other genotypic data structures in said plurality of genotypic data structures using a suitably programmed computer; wherein the loci that correspond to said one or more genotypic data structures represent said one or more candidate chromosomal regions that associate with said phenotype and wherein an amount of said genome that is included in each locus in said plurality of loci is predetermined at a time prior to said identifying step;

wherein each respective genotypic data structure in said plurality of genotypic data structures comprises a plurality of elements and each element in each respective genotypic data structure in said plurality of genotypic data structures corresponds to a difference of at least one component of said locus corresponding to the respective genotypic data structure; wherein, for each element in each respective genotypic data structure in said plurality of genotypic data structures, said different strains of said species are selected from a plurality of strains of said species;

wherein an amount that a variation contributes to said at least one component of a locus corresponding to a genotypic data structure in said plurality of genotypic data structures is a function of a distance said variation is away from a center of the locus; and wherein a genotypic data structure in said plurality of genotypic data structures comprises a plurality of variations that are distributed about the center of a locus corresponding to the genotypic data structure, and said establishing step further comprises:

fitting a distribution of said plurality of variations about the center of said locus with a probability function; and weighting each variation by a corresponding value derived from said probability function such that variations further from the center of said locus are downweighted so that they contribute less to said genotypic data structure than variations that are closer to said center of said locus; and communicating said one or more genotypic data structures to a user, a display, a readily accessible computer memory or other computer on a network.

2. The method of claim 1 wherein said probability function is a Gaussian probability distribution, a Poisson distribution, or a Lorentzian distribution.

3. A method of associating a phenotype with one or more candidate chromosomal regions in a genome of a species using a phenotypic data structure that comprises a difference in said phenotype between different strains of said species, said genome including a plurality of loci, said method comprising:

establishing a genotypic data structure using a suitably programmed computer, said genotypic data structure corresponding to a locus in said plurality of loci, said genotypic data structure comprising a variation of at least one component of said locus between different strains of said species;

determining a correlation value for said genotypic data structure by a comparison of said phenotypic data structure with said genotypic data structure using a suitably programmed computer;

repeating said establishing and determining steps for each locus in said plurality of loci using a suitably programmed computer, thereby establishing a plurality of genotypic data structures and, for each respective genotypic data structure in the plurality of genotypic data structures, determining a correlation value;

identifying one or more genotypic data structures in said plurality of genotypic data structures that have correlation values that are higher than the correlation values for all other genotypic data structures in said plurality of genotypic data structures using a suitably programmed computer;

wherein the loci that correspond to said one or more genotypic data structures represent said one or more candidate chromosomal regions that associate with said phenotype and wherein an amount of said genome that is included in each locus in said plurality of loci is predetermined at a time prior to said identifying step; wherein said correlation value is formed in accordance with the expression:

$$c(P, G^L) = \frac{\sum^i (p(i) - <P>)(g(i) - <G^L>)}{\left\{ [\sum^i (p(i) - <P>)^2][\sum^i (g(i) - <G^L>)^2] \right\}^{1/2}}$$

where, $c(P, G^L)$ is said correlation value;

$p(i)$ is a value of the $i^{th}$ element of said phenotypic data structure;

$g(i)$ is a value of the $i^{th}$ element of said genotypic data structure;

$<P>$ is a mean value of all elements in said phenotypic data structure; and $<G^L>$ is a mean value of all elements in said genotypic data structure; and communicating said one or more genotypic data structures to a user, a display, a readily accessible computer memory or other computer on a network.

4. A method of associating a phenotype with one or more candidate chromosomal regions in a genome of a species using a phenotypic data structure that comprises a difference in said phenotype between different strains of said species, said genome including a plurality of loci, said method comprising:

establishing a genotypic data structure using a suitably programmed computer, said genotypic data structure corresponding to a locus in said plurality of loci, said genotypic data structure comprising a variation of at least one component of said locus between different strains of said species;

determining a correlation value for said genotypic data structure by a comparison of said phenotypic data structure with said genotypic data structure using a suitably programmed computer;

repeating said establishing and determining steps for each locus in said plurality of loci using a suitably programmed computer, thereby establishing a plurality of genotypic data structures and, for each respective genotypic data structure in the plurality of genotypic data structures, a correlation value;

identifying one or more genotypic data structures in said plurality of genotypic data structures that have correlation values that are higher than the correlation values for all other genotypic data structures in said plurality of genotypic data structures using a suitably programmed computer;

wherein the loci that correspond to said one or more genotypic data structures represent said one or more candidate chromosomal regions that associate with said phenotype and wherein an amount of said genome that is included in each locus in said plurality of loci is predetermined at a time prior to said identifying step; wherein said correlation value is formed in accordance with the expression $$c(P, G^L) = \frac{\left[\sum^i (p(i) - <P>)(g(i) - <G^L>)\right] \times Z}{\left\{[\sum^i (p(i) - <P>)^2][\sum^i (g(i) - <G^L>)^2]\right\}^{1/2}}$$

where, $c(P, G^L)$ is said correlation value;

$p(i)$ is a value of the $i^{th}$ element of said phenotypic data structure;

$g(i)$ is a value of the $i^{th}$ element of said genotypic data structure;

$<P>$ is a mean value of all elements in said phenotypic data structure;

$<G^L>$ is a mean value of all elements in said genotypic data structure; and

Z is a function of a number of components in the locus, corresponding to the genotypic data structure, having a variation between different strains of said species; and communicating said one or more genotypic data structures to a user, a display, a readily accessible computer memory or other computer on a network.

5. The method of claim 4, wherein said function is selected from the group consisting of taking the square root of Z, squaring Z, raising Z by the power of a positive integer, taking a logarithm of Z, and taking an exponential of Z.

6. A method of associating a phenotype with one or more candidate chromosomal regions in a genome of a species using a phenotypic data structure that comprises a difference in said phenotype between different strains of said species, said genome including a plurality of loci, said method comprising:

establishing a genotypic data structure using a suitably programmed computer, said genotypic data structure corresponding to a locus in said plurality of loci, said genotypic data structure comprising a variation of at least one component of said locus between different strains of said species;

determining a correlation value for said genotypic data structure base on a comparison of said phenotypic data structure with said genotypic data structure using a suitably programmed computer;

repeating said establishing and determining steps for each locus in said plurality of loci using a suitably programmed computer, thereby establishing a plurality of genotypic data structures and, for each respective genotypic data structure in the plurality of genotypic data structures, a correlation value;

identifying one or more genotypic data structures in said plurality of genotypic data structures that have correlation values that are higher than the correlation values for all other genotypic data structures in said plurality of genotypic data structures using a suitably programmed computer;

wherein the loci that correspond to said one or more genotypic data structures represent said one or more candidate chromosomal regions that associate with said phenotype and wherein an amount of said genome that is included in each locus in said plurality of loci is predetermined at a time prior to said identifying step; wherein said correlation value is a correlative measure $cm$ that is computed in accordance with the expression:

$$cm(P, G^L) = \frac{\left[\sum^i (p(i) - <P>)(g(i) - <G^L>)\right]}{\left\{[\sum^i (p(i) - <P>)^2]\right\}^{1/2}}$$

where, $cm(P, G^L)$ is said correlative measure;

$p(i)$ is a value of the $i^{th}$ element of said phenotypic data structure;

$g(i)$ is a value of the $i^{th}$ element of said genotypic data structure;

$<P>$ is a mean value of all elements in said phenotypic data structure; and $<G^L>$ is a mean value of all elements in said genotypic data structure; and communicating said one or more genotypic data structures to a user, a display, a readily accessible computer memory or other computer on a network.

7. A computer program product for use in conjunction with a computer system, the computer program product comprising a physical computer readable storage medium and a computer program mechanism embedded therein, the computer program mechanism comprising:

a genotypic database for storing variations in genomic sequences of a plurality of strains of a species;

a phenotypic data structure, said phenotypic data structure comprising a difference in a phenotype between different strains of said species; and a program module for associating said phenotype with one or more candidate chromosomal regions in a genome of said species, said genome including a plurality of loci, said program module comprising:

instructions for establishing a genotypic data structure, said genotypic data structure corresponding to a locus in said plurality of loci, said genotypic data structure comprising a variation of at least one component of said locus between different strains of said species stored in said genotypic database;

instructions for determining a correlation value for said genotypic data structure by a comparison of said phenotypic data structure with said genotypic data structure;

instructions for repeating said instructions for establishing and said instructions for determining, for each locus in said plurality of loci, thereby establishing a plurality of genotypic data structures and, for each respective genotypic data structure in the plurality of genotypic data structures, determining a correlation value;

instructions for identifying one or more genotypic data structures in said plurality of genotypic data structures that have correlation values that are higher than the correlation values for all other genotypic data structures in said plurality of genotypic data structures; wherein the loci that correspond to said one or more genotypic data structures represent said one or more candidate chromosomal regions that associate with said phenotype and wherein an amount of said genome that is included in each locus in said plurality of loci is predetermined at a time prior to said identifying step; wherein each said genotypic data structure in said plurality of genotypic data structures comprises a plurality of variations that are distributed about the center of a locus corresponding to the genotypic data structure, and said instructions for establishing further comprise:

instructions for fitting a distribution of said plurality of variations about the center of said locus with a probability function; and instructions for weighting each variation by a corresponding value derived from said probability function such that variations further from the center of said locus are downweighted so that they contribute less to said genotypic data structure than loci that are closer to said center of said corresponding locus; and instructions for communicating said one or more genotypic data structures to a user, a display, a readily accessible computer memory or other computer on a network.

8. The computer program product of claim 7 wherein said probability function is a Gaussian probability distribution, a Poisson distribution, or a Lorentzian distribution.

9. A computer program product for use in conjunction with a computer system, the computer program product comprising a physical computer readable storage medium and a computer program mechanism embedded therein, the computer program mechanism comprising:

a genotypic database for storing variations in genomic sequences of a plurality of strains of a species;

a phenotypic data structure, said phenotypic data structure comprising a difference in a phenotype between different strains of said species; and a program module for associating said phenotype with one or more candidate chromosomal regions in a genome of said species, said genome including a plurality of loci, said program module comprising:

instructions for establishing a genotypic data structure, said genotypic data structure corresponding to a locus in said plurality of loci, said genotypic data structure comprising a variation of at least one component of said locus between different strains of said species stored in said genotypic database;

instructions for determining a correlation value for said genotypic data structure by a comparison of said phenotypic data structure with said genotypic data structure;

instructions for repeating said instructions for establishing and said instructions for determining, for each locus in said plurality of loci, thereby establishing a plurality of genotypic data structures and, for each respective genotypic data structure in the plurality of genotypic data structures, determining a correlation value;

instructions for identifying one or more genotypic data structures in said plurality of genotypic data structures that have correlation values that are higher than the correlation values for all other genotypic data structures in said plurality of genotypic data structures; wherein the loci that correspond to said one or more genotypic data structures represent said one or more candidate chromosomal regions that associate with said phenotype and wherein an amount of said genome that is included in each locus in said plurality of loci is predetermined at a time prior to said identifying step, and wherein said instructions for determining include instructions for forming said correlation value in accordance with the expression:

$$c(P, G^L) = \frac{\sum^{i}(p(i) - <P>)(g(i) - <G^L>)}{\{[\sum^i (p(i) - <P>)^2][\sum^i (g(i) - <G^L>)^2]\}^{1/2}}$$

where, c(P, $G^L$) is said correlation value;

p(i) is a value of the $i^{th}$ element of said phenotypic data structure;

g(i) is a value of the $i^{th}$ element of said genotypic data structure;

<P> is a mean value of all elements in said phenotypic data structure; and

<$G^L$> is a mean value of all elements in said genotypic data structure; and instructions for communicating said one or more genotypic data structures to a user, a display, a readily accessible computer memory or other computer on a network.

10. A computer program product for use in conjunction with a computer system, the computer program product comprising a physical computer readable storage medium and a computer program mechanism embedded therein, the computer program mechanism comprising:

a genotypic database for storing variations in genomic sequences of a plurality of strains of a species;

a phenotypic data structure, said phenotypic data structure comprising a difference in a phenotype between different strains of said species; and a program module for associating said phenotype with one or more candidate chromosomal regions in a genome of said species, said genome including a plurality of loci, said program module comprising:

instructions for establishing a genotypic data structure, said genotypic data structure corresponding to a locus in said plurality of loci, said genotypic data structure comprising a variation of at least one component of said locus between different strains of said species stored in said genotypic database;

instructions for determining a correlation value for said genotypic data structure by a comparison of said phenotypic data structure with said genotypic data structure;

instructions for repeating said instructions for establishing and said instructions for determining, for each locus in said plurality of loci, thereby establishing a plurality of genotypic data structures and, for each respective genotypic data structure in the plurality of genotypic data structures, determining a correlation value;

instructions for identifying one or more genotypic data structures in said plurality of genotypic data structures that have correlation values that are higher than the correlation values for all other genotypic data structures in said plurality of genotypic data structures; wherein the loci that correspond to said one or more genotypic data structures represent said one or more candidate chromosomal regions that associate with said phenotype and wherein an amount of said genome that is included in each locus in said plurality of loci is predetermined at a time prior to said identifying step, and wherein said instructions for determining include instructions for forming said correlation value in accordance with the expression:

$$c(P, G^L) = \frac{\left[\sum^i (p(i) - <P>)(g(i) - <G^L>)\right] \times Z}{\{[\sum^i (p(i) - <P>)^2][\sum^i (g(i) - <G^L>)^2]\}^{1/2}}$$

where,
$c(P, G^L)$ is said correlation value;
$p(i)$ is a value of the $i^{th}$ element of said phenotypic data structure;
$g(i)$ is a value of the $i^{th}$ element of said genotypic data structure;
<P> is a mean value of all elements in said phenotypic data structure;
<$G^L$> is a mean value of all elements in said genotypic data structure; and
Z is a function of a number of components in the locus corresponding to the genotypic structure, having a variation between different strains of said species; and
instructions for communicating said one or more genotypic data structures to a user, a display, a readily accessible computer memory or other computer on a network.

11. A computer program product for use in conjunction with a computer system, the computer program product comprising a physical computer readable storage medium and a computer program mechanism embedded therein, the computer program mechanism comprising:
a genotypic database for storing variations in genomic sequences of a plurality of strains of a species;
a phenotypic data structure, said phenotypic data structure comprising a difference in a phenotype between different strains of said species; and
a program module for associating said phenotype with one or more candidate chromosomal regions in a genome of said species, said genome including a plurality of loci, said program module comprising:
instructions for establishing a genotypic data structure, said genotypic data structure corresponding to a locus in said plurality of loci, said genotypic data structure comprising a variation of at least one component of said locus between different strains of said species stored in said genotypic database;
instructions for determining a correlation value for said genotypic data structure by a comparison of said phenotypic data structure with said genotypic data structure;
instructions for repeating said instructions for establishing and said instructions for determining, for each locus in said plurality of loci, thereby establishing a plurality of genotypic data structures and, for each respective genotypic data structure in the plurality of genotypic data structures, determining a correlation value;
instructions for identifying one or more genotypic data structures in said plurality of genotypic data structures that have correlation values that are higher than the correlation values for all other genotypic data structures in said plurality of genotypic data structures; wherein the loci that correspond to said one or more genotypic data structures represent said one or more candidate chromosomal regions that associate with said phenotype and wherein an amount of said genome that is included in each locus in said plurality of loci is predetermined at a time prior to said identifying step, and wherein said instructions for determining include instructions for forming said correlation value in accordance with a correlative measure $cm$ that is computed in accordance with the expression:

$$cm(P, G^L) = \frac{\left[\sum^i (p(i) - <P>)(g(i) - <G^L>)\right]}{\{[\sum^i (p(i) - <P>)^2]\}^{1/2}}$$

where,
$cm(P, G^L)$ is said correlative measure;
$p(i)$ is a value of the $i^{th}$ element of said phenotypic data structure;
$g(i)$ is a value of the $i^{th}$ element of said genotypic data structure;
<P> is a mean value of all elements in said phenotypic data structure; and
<$G^L$> is a mean value of all elements in said genotypic data structure; and
instructions for communicating said one or more genotypic data structures to a user, a display, a computer memory or other computer on a network.

12. A computer system for associating a phenotype with one or more candidate chromosomal regions in a genome of a species, said genome including a plurality of loci, the computer system comprising:
a central processing unit;
a memory, coupled to the central processing unit, the memory storing:
a genotypic database for storing variations in genomic sequences of a plurality of strains of said species;
a phenotypic data structure that comprises a difference in said phenotype between different strains of said species; and
a program module, said program module comprising:
instructions for establishing a genotypic data structure, said genotypic data structure corresponding to a locus in said plurality of loci, said genotypic data structure comprising a variation of at least one component of said locus between different strains of said species stored in said genotypic database;
instructions for determining a correlation value for said genotypic data structure by a comparison of said phenotypic data structure with said genotypic data structure;
instructions for repeating said instructions for establishing and said instructions for determining, for each locus in said plurality of loci, thereby establishing a plurality of genotypic data structures and, for each respective genotypic data structure in the plurality of genotypic data structures, determining a correlation value;
instructions for identifying one or more genotypic data structures in said plurality of genotypic data structures that have correlation values that are higher than the correlation values for all other genotypic data structures in said plurality of genotypic data structures; wherein the loci that correspond to said one or more genotypic data structures represent said one or more candidate chromosomal regions that associate with said phenotype and wherein an amount of said genome that is included in each locus in said plurality of loci is predetermined at a time prior to said identifying step, and wherein said instructions for determining include instructions for forming said correlation value in accordance with the expression:

$$c(P, G^L) = \frac{\sum^i (p(i) - <P>)(g(i) - <G^L>)}{\{[\sum^i (p(i) - <P>)^2][\sum^i (g(i) - <G^L>)^2]\}^{1/2}}$$

where, $c(P, G^L)$ is said correlation value;

$p(i)$ is a value of the $i^{th}$ element of said phenotypic data structure;

$g(i)$ is a value of the $i^{th}$ element of said genotypic data structure;

$<P>$ is a mean value of all elements in said phenotypic data structure; and $<G^L>$ is a mean value of all elements in said genotypic data structure; and instructions for communicating said one or more genotypic data structures to a user, a display, a readily accessible computer memory or other computer on a network.

\* \* \* \* \*